US007033789B1

(12) United States Patent
Hamelin et al.

(10) Patent No.: US 7,033,789 B1
(45) Date of Patent: Apr. 25, 2006

(54) **DNA MOLECULES ENCODING L-GLUTAMATE-GATED CHLORIDE CHANNELS FROM *SCHISTOCERCA AMERICANA***

(75) Inventors: Michel J. Hamelin, Jersey City, NJ (US); Jeffrey W. Warmke, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 416 days.

(21) Appl. No.: 10/111,161

(22) PCT Filed: Oct. 19, 2000

(86) PCT No.: PCT/US00/28936

§ 371 (c)(1), (2), (4) Date: Apr. 19, 2002

(87) PCT Pub. No.: WO01/30849

PCT Pub. Date: May 3, 2001

Related U.S. Application Data

(60) Provisional application No. 60/160,877, filed on Oct. 22, 1999.

(51) Int. Cl.
*C07K 14/705* (2006.01)
*C12N 5/10* (2006.01)
*C12N 15/12* (2006.01)
*C12N 15/63* (2006.01)

(52) U.S. Cl. ................... 435/69.1; 435/71.1; 435/71.2; 435/252.3; 435/254.11; 435/320.1; 435/325; 435/471; 530/350

(58) Field of Classification Search ............... 536/23.1, 536/23.5; 530/350; 435/69.1, 71.1, 71.2, 435/252.3, 254.11, 320.1, 471, 325
See application file for complete search history.

(56) References Cited

U.S. PATENT DOCUMENTS 5,527,703 A 6/1996 Cully et al.

OTHER PUBLICATIONS

Eck & Wilson in Goodman & Gilman's The Pharmacological Basis of Therapeutics, Ninth Edition, McGraw-Hill New York, 1996.*

Mikayama et al. Proc. Natl. Acad. Sci. USA vol. 90, pp. 10056-10060.*

Voet et al. Biochemistry John Wiley & Sons, Inc., pp. 126-128 and 228-234.*

Dudel, etal.: "Chloride channels gated by extrajunctional glutamate receptors (H-receptors) on locust leg muscle"; Brain Research, vol. 481, pp. 215-220, 1989.

Lingel, etal.: "A glutamate-activated chloride conductance on a crustacean muscle"; Brain Research, vol. 212, pp. 481-488, 1981.

Horseman, etal.: "The effects of L-glutamate on cultured insect neurones"; Neurosciences Letters, vol. 85, pp. 65-70, 1988.

Wafford and Sattelle.: "L-Glutamate Receptors on the Cell Body Membrane of an Identified Insect Motor Neurone"; J. Exp. Biol., vol. 144, pp. 449-462, 1989.

Lea and Usherwood.: "The Site of Action of Ibotenic Acid and the Indentification of Two Populations of Glutamate Receptors on Insect Muscle-Fibres"; Comp. Gen. Pharmac., vol. 4, pp. 333-350, 1973.

Cullcandy.: "Two Types of Extrajunctional L.-Glutamate Receptors in Locust Muscle Fibres"; J. Physiol., vol. 255, pp. 449-464, 1976.

Cully, etal.: "Cloning of an avermetinsensitive glutamate-gated chloride channel from *Caenorhabditis elegans*"; Nature, vol. 371, pp. 707-711, 1994.

Arena, etal.: "Expression of a Glutamate-activated Chloride current in *Xenopus oocytes* injected with *Caenorhabditis elegans* RNA; evidence of modulation by avermectin"; Molecular Brain Research, vol. 15, pp. 339-348, 1992.

Cully, etal.: "Identification of a *Drosophila melanogaster* Glutamate-gated chloride Channel Sensitive to the Antiparasitic Agent Avermectin"; J. Biol. Chem., vol. 271, pp. 20187-20191, 1996.

Raymond, etal.: "Co-existence in DUM neurones of two GluCl channels that differ in their picrotoxin sensitivity", Neuropharmacology, vol. 11, No. 12, 1pp. 2695-2701, 2000.

* cited by examiner

*Primary Examiner*—Prema Mertz
(74) *Attorney, Agent, or Firm*—Yang Xu; Jack L. Tribble

(57) ABSTRACT

The present invention relates in part to isolated nucleic acid molecules (polynucleotides) which encode *Schistocerca americana* (grasshopper) glutamate-gated chloride channels. The present invention also relates to recombinant vectors and recombinant hosts which contain a DNA fragment encoding *S. americana* glutamate-gated chloride channels, substantially purified forms of associated *S. americana* glutamate-gated chloride channels and recombinant membrane fractions comprising these proteins, associated mutant proteins, and methods associated with identifying compounds which modulate associated *Schistocerca americana* glutamate-gated chloride channels, which will be useful as insecticides.

18 Claims, 10 Drawing Sheets

```
       1                                                      50
Sa1LA_ .......... ........GC CGCACGTGCC GCACGCCTCG CCACGCCGCA
Sa1LC_ .......... ........GC CGCACGTGCC GCACGCCTCG CCACGCCGCA
Sa1SA_ AGCAGTGGCG CGACTACCGC CGCACGTGCC GCACGCCTCG CCACGCCGCA
Sa1SC_ AGCAGTGGCG CGACTACCGC CGCACGTGCC GCACGCCTCG CCACGCCGCA
Sa2_   .......... .......... .......... .......... ..........

       51                                                    100
Sa1LA_ CCGCAGGTCT CTTCGCCCAT GGAGGAGCTC GTGCGACTGG AGTGAGCTTG
Sa1LC_ CCGCAGGTCT CTTCGCCCAT GGAGGAGCTC GTGCGACTGG AGTGAGCTTG
Sa1SA_ CCGCAGGTCT CTTCGCTCAT GGAGGAGCTC GTGCGACTGG AGTGAGCGTG
Sa1SC_ CCGCAGGTCT CTTCGCTCAT GGAGGAGCTC GTGCGACTGG AGTGAGCGTG
Sa2_   .......... .......... .......... .......... ..........

       101                                                   150
Sa1LA_ TGGCTTACGG CTCTATCCGA GGAACCATAA GCAA..GTCA CCGGCAGTTG
Sa1LC_ TGGCTTACGG CTCTATCCGA GGAACCATAA GCAA..GTCA CCGGCAGTTG
Sa1SA_ TGGCTTACGG CTCTATCCGA GGAACCATAA GCAACAGTCA CCGGCAGTTG
Sa1SC_ TGGCTTACGG CTCTATCCGA GGAACCATAA GCAACAGTCA CCGGCAGTTG
Sa2_   .......... .......... .......... .......... ..........

       151                                                   200
Sa1LA_ AGGGTTAACT GGTAATGCGG GCGCGGGTCG AGGCCAGCAG AGACCGCCGC
Sa1LC_ AGGGTTAACT GGTAATGCGG GCGCGGGTCG AGGCCAGCAG AGACCGCCGC
Sa1SA_ AGGGTTAACT GGTAATGCGG GCGCGGGTCG AGGCCAGCAG AGACCGCCGC
Sa1SC_ AGGGTTAACT GGTAATGCGG GCGCGGGTCG AGGCCAGCAG AGACCGCCGC
Sa2_   .......... .......... .......... .......... ..........

       201                                                   250
Sa1LA_ GTGCCGCCCG CGGACTCGCA CTGCCCCCCG GACGCGCCGC CCCGGCCGCC
Sa1LC_ GTGCCGCCCG CGGACTCGCA CTGCCCCCCG GACGCGCCGC CCCGGCCGCC
Sa1SA_ GTGCCGCCCG CGGACTCGCA CTGCCCCCCG GACGCGCCGC CCCGGCCGCC
Sa1SC_ GTGCCGCCCG CGGACTCGCA CTGCCCCCCG GACGCGCCGC CCCGGCCGCC
Sa2_   .......... .......... .......... .......... ..........

       251                                                   300
Sa1LA_ AGCCGCGCGC TCGCCCTGCT CCCACCGCCT CTGAAGTTCG AGGGACAGCT
Sa1LC_ AGCCGCGCGC TCGCCCTGCT CCCACCGCCT CTGAAGTTCG AGGGACAGCT
Sa1SA_ AGCCGCGCGC TCGCCCTGCT CCCGCCGCCT CTGAAGTCCA AGGGTTAGCT
Sa1SC_ AGCCGCGCGC TCGCCCTGCT CCCGCCGCCT CTGAAGTCCA AGGGTTAGCT
Sa2_   .......... .......... .......... ....GGCACG AGGG.CGTCT

       301                                                   350
Sa1LA_ CAGCCTCAGC ATCCCTACAG GAACCATGAT GAGCGACCTC TGCAAGACGC
Sa1LC_ CAGCCTCAGC ATCCCTACAG GAACCATGAT GAGCGACCTC TGCAAGACGC
Sa1SA_ CAGCCTCAGC ATCCCTGCAG GAACCATGAT GAGCGACCTC TGCAAGACGC
Sa1SC_ CAGCCTCAGC ATCCCTGCAG GAACCATGAT GAGCGACCTC TGCAAGACGC
Sa2_   CGGCTGTCCA CACACAGCAG GAATCATGCT GAGCGCAACA CCCAGCAAGC
```

FIG.1A

```
        351                                                    400
Sa1LA_  CGTGGTGGCT TTGTGCGCTG CTGTTGCTGG CCGCCAACGT GCCAGATGCC
Sa1LC_  CGTGGTGGCT TTGTGCGCTG CTGTTGCTGG CCGCCAACGT GCCAGATGCC
Sa1SA_  CGTGGTGGCT TTGTGCGCTG CTGTTGCTGG CCGCCAACGT GCCAGATGCC
Sa1SC_  CGTGGTGGCT TTGTGCGCTG CTGTTGCTGG CCGCCAACGT GCCAGATGCC
Sa2_    TGCGGCGATT TTGTGCTTTG GTGCTGTTGG TTGTGAATCT GTCAAAAGTC

        401                                                    450
Sa1LA_  TGGTGCACGC AGCAGAAGAT GAACTTCCGC GAGAAGGAGA AACAGGTGCT
Sa1LC_  TGGTGCACGC AGCAGAAGAT GAACTTCCGC GAGAAGGAGA AACAGGTGCT
Sa1SA_  TGGTGCACGC AGCAGAAGAT GAACTTCCGC GAGAAGGAGA AACAGGTGCT
Sa1SC_  TGGTGCACGC AGCAGAAGAT GAACTTCCGC GAGAAGGAGA AACAGGTGCT
Sa2_    ACATGCTCGG ATCAGAAGAC TAACATCCGG GAGGCGGAGA GGCAGGTGAT

        451                                                    500
Sa1LA_  GGACCAGATC CTGGGGCCAG GTCGCTACGA CGCGCGCATC CGGCCGTCGG
Sa1LC_  GGACCAGATC CTGGGGCCAG GTCGCTACGA CGCGCGCATC CGGCCGTCGG
Sa1SA_  GGACCAGATC CTGGGGCCAG GTCGCTACGA CGCTCGCATC CGGCCGTCGG
Sa1SC_  GGACCAGATC CTGGGGCCAG GTCGCTACGA CGCTCGCATC CGGCCGTCGG
Sa2_    GGAGCACGTC CTGAGCCCGA GCCGCTACGA CGCGCGGCTG CGGCCCCCGG

        501                                                    550
Sa1LA_  GGATCAACGG CACAGCGGAC AACCCCACCA TAGTGAAAGT GAACATCTTC
Sa1LC_  GGATCAACGG CACAGCGGAC AACCCCACCA TAGTGAAAGT GAACATCTTC
Sa1SA_  GGATCAACGG CACAGCGGAC AACCCCACCA TAGTGAAAGT GAACATCTTC
Sa1SC_  GGATCAACGG CACAGCGGAC AACCCCACCA TAGTGAAAGT GAACATCTTC
Sa2_    GATACAACGG CACAG...AG AGTCCCACTG TGGTAAAAGT TAACATCTTT

        551                                                    600
Sa1LA_  CTTCGCTCTA TCAGCAAAAT AGACGATTAT AAAATGATGT TCCGCTGCGC
Sa1LC_  CTTCGCTCTA TCAGCAAAAT AGACGATTAT AAAATGATGT TCCGCTGCGC
Sa1SA_  CTTCGCTCTA TCAGCAAAAT AGACGATTAT AAAATG.... ..........
Sa1SC_  CTTCGCTCTA TCAGCAAAAT AGACGATTAT AAAATG.... ..........
Sa2_    GTACGCTCCA TCAGCAGAGT AGATGATCAG CATATG.... ..........

        601                                                    650
Sa1LA_  TGCCCCGCTT GCATGCCGCC CGGACCCCGC ACGCCGCCCT CGGCCCAGCG
Sa1LC_  TGCCCCGCTT GCATGCCGCC CGGACCCCGC ACGCCGCCCT CGGCCCAGCG
Sa1SA_  .......... .......... .......... .......... ..........
Sa1SC_  .......... .......... .......... .......... ..........
Sa2_    .......... .......... .......... .......... ..........

        651                                                    700
Sa1LA_  TCATGTGTTT TGTTACACGT GTTCTCAACA GGAGCCAGGC TCACCGACCC
Sa1LC_  TCATGTGTTT TGTTACACGT GTTCTCAACA GGAGCCAGGC TCACCGACCC
Sa1SA_  .......... .......... .......... .......... ..........
Sa1SC_  .......... .......... .......... .......... ..........
Sa2_    .......... .......... .......... .......... ..........
```

FIG. 1B

```
        701                                                750
Sa1LA_  GGCCGCCAAT CAGGCGCCGC GTGTGCGACT CCGAACAAGG AATACAGCGT
Sa1LC_  GGCCGCCAAT CAGGCGCCGC GTGTGCGACT CCGAACAAGG AATACAGCGT
Sa1SA_  .......... .......... .......... .........G AATACAGCGT
Sa1SC_  .......... .......... .......... .........G AATACAGCGT
Sa2_    .......... .......... .......... .........G AATATGACGC

        751                                                800
Sa1LA_  CCAGCTGACA TTCAGAGAGC AGTGGATGGA TGAGCGGCTC AAGTTCAATG
Sa1LC_  CCAGCTGACA TTCAGAGAGC AGTGGATGGA TGAGCGGCTC AAGTTCAATG
Sa1SA_  CCAGCTGACA TTCAGAGAGC AGTGGATGGA TGAGCGGCTC AAGTTCAATG
Sa1SC_  CCAGCTGACA TTCAGAGAGC AGTGGATGGA TGAGCGGCTC AAGTTCAATG
Sa2_    GCAGTTGACG TTCAGAGAGC AGTGGTTTGA CGACAGGCTC AAGTTTGACG

        801                                                850
Sa1LA_  ACTTCAAAGG AAAAATAAAG TACCTGACAC TGACAGACGC CAACAGAGTA
Sa1LC_  ACTTCAAAGG AAAAATAAAG TACCTGACAC TGACAGACGC CAACAGAGTA
Sa1SA_  ACTTCAAAGG AAAAATAAAG TACCTGACAC TGACAGACGC CAACAGAGTA
Sa1SC_  ACTTCAAAGG AAAAATAAAG TACCTGACAC TGACAGACGC CAACAGAGTA
Sa2_    ATTTTGGAGG TAAAATCAAA TATCTAACAC TGACAGATCC CAGCAGAATA

        851                                                900
Sa1LA_  TGGATGCCAG ATTTATTTTT CTCTAACGAA AAGGAAGGAC ATTTTCATAA
Sa1LC_  TGGATGCCAG ATTTATTTTT CTCTAACGAA AAGGAAGGAC ATTTTCATAA
Sa1SA_  TGGATGCCAG ATTTATTTTT CTCTAACGAA AAGGAAGGAC ATTTTCATAA
Sa1SC_  TGGATGCCAG ATTTATTTTT CTCTAACGAA AAGGAAGGAC ATTTTCATAA
Sa2_    TGGATGCCAG ATTTATTTTT TAGCAACGAG AAGAAAGCAC ACTTTCACGA

        901                                                950
Sa1LA_  CATTATCATG CCCAACGTTT ATATACGTAT TTTTCCTTAT GGATCGGTGC
Sa1LC_  CATTATCATG CCCAACGTTT ATATACGTAT TTTTCCTTAT GGATCGGTGC
Sa1SA_  CATTATCATG CCCAACGTTT ATATACGTAT TTTTCCTTAT GGATCGGTGC
Sa1SC_  CATTATCATG CCCAACGTTT ATATACGTAT TTTTCCTTAT GGATCGGTGC
Sa2_    TGTAGTAATG CCTAATGTCT ATGTACGAAT ATTTCCTCTT GGGTCGGTTC

        951                                               1000
Sa1LA_  TCTACAGTAT CAGAATCTCT CTGACSCTCT CCTGCCCGAT GAACCTGAAG
Sa1LC_  TCTACAGTAT CAGAATCTCT CTGACSCTCT CCTGCCCGAT GAACCTGAAG
Sa1SA_  TCTACAGTAT CAGAATCTCT CTGACGCTCT CCTGCCCGAT GAACCTGAAG
Sa1SC_  TCTACAGTAT CAGAATCTCT CTGACGCTCT CCTGCCCGAT GAACCTGAAG
Sa2_    TCTACAGTAC CAGAATCTCA ATGACACTCT CGTGTCCCAT GGACCTGAGG

        1001                                              1050
Sa1LA_  CTGTACCCGC TCGACAGGCA GGTCTGCTCG CTGAGGATGG CCAGCTATGG
Sa1LC_  CTGTACCCGC TCGACAGGCA GGTCTGCTCG CTGAGGATGG CCAGCTATGG
Sa1SA_  CTGTACCCGC TCGACAGGCA GGTCTGCTCG CTGAGGATGG CCAGCTATGG
Sa1SC_  CTGTACCCGC TCGACAGGCA GGTCTGCTCG CTGAGGATGG CCAGCTATGG
Sa2_    CTGTACCCAC ACGATCGACA GGTGTGCTCC ATCAGGATGG CCAGCTATGG
```

FIG. 1C

```
        1051                                                   1100
Sa1LA_  TTGGACGACT GATGACCTGG TGTTCCTGTG GAAAGACGGC GACCCGGTGC
Sa1LC_  TTGGACGACT GATGACCTGG TGTTCCTGTG GAAAGACGGC GACCCGGTGC
Sa1SA_  TTGGACGACT GATGACCTGG TGTTCCTGTG GAAAGACGGC GACCCGGTGC
Sa1SC_  TTGGACGACT GATGACCTGG TGTTCCTGTG GAAAGACGGC GACCCGGTGC
Sa2_    TTGGACGACT GAAGACCTGG TGTTCATGTG GAAAGACGGC GACCCGGTGC

        1101                                                   1150
Sa1LA_  AGGTGGTCAA GAACCTGCAC CTGCCGCGCT TCACGCTAGA GAAGTTCCTT
Sa1LC_  AGGTGGTCAA GAACCTGCAC CTGCCGCGCT TCACGCTAGA GAAGTTCCTT
Sa1SA_  AGGTGGTCAA GAACCTGCAC CTGCCGCGCT TCACGCTAGA GAAGTTCCTT
Sa1SC_  AGGTGGTCAA GAACCTGCAC CTGCCGCGCT TCACGCTAGA GAAGTTCCTT
Sa2_    AGGTGGTCAA GAACCTGCGC CTTCCACGCT TCACGCTAGA GAAGTTCGTT

        1151                                                   1200
Sa1LA_  ACCGACTACT GCAACAGCAA AACTAACACA GGAGAGTACA GCTGCTTGAA
Sa1LC_  ACCGACTACT GCAACAGCAA AACTAACACA GGAGAGTACA GCTGCTTGAA
Sa1SA_  ACCGACTACT GCAACAGCAA AACCAACACA GGAGAGTACA GCTGCTTGAA
Sa1SC_  ACCGACTACT GCAACAGCAA AACCAACACA GGAGAGTACA GCTGCTTGAA
Sa2_    ACTGATTACT GCCACGCCAG GACAAACACA GGCGAGTACA GCTGCCTTAA

        1201                                                   1250
Sa1LA_  GGTGGACCTG CTGTTCAAGC GCGAGTTCAG CTACTACCTG ATCCAGATCT
Sa1LC_  GGTGGACCTG CTGTTCAAGC GCGAGTTCAG CTACTACCTG ATCCAGATCT
Sa1SA_  GGTGGACCTG CTGTTCAAGC GCGAGTTCAG CTACTACCTG ATCCAGATCT
Sa1SC_  GGTGGACCTG CTGTTCAAGC GCGAGTTCAG CTACTACCTG ATCCAGATCT
Sa2_    AGTGGAACTG GTGTTTAAAC GCGAGTTCCG CTACTACATG GTGCACATCT

        1251                                                   1300
Sa1LA_  ACATCCCGTG CTGCATGCTG GTGATAGTGT CGTGGGTGTC CTTCTGGCTC
Sa1LC_  ACATCCCGTG CTGCATGCTG GTGATAGTGT CGTGGGTGTC CTTCTGGCTC
Sa1SA_  ACATCCCGTG CTGCATGCTG GTGATAGTGT CGTGGGTGTC CTTCTGGCTC
Sa1SC_  ACATCCCGTG CTGCATGCTG GTGATAGTGT CGTGGGTGTC CTTCTGGCTC
Sa2_    ACATTCCGAC TTTCATGCTG GTGATAGTGT CGTGGCTATC GTTCTGGCTG

        1301                                                   1350
Sa1LA_  GATCAGAGCG CCATCCCGGC ACGGGTGTCC CTAGGCGTGA CCACGCTGCT
Sa1LC_  GATCAGAGCG CCATCCCGGC ACGGGTGTCC CTAGGCGTGA CCACGCTGCT
Sa1SA_  GATCAGAGCG CCATCCCGGC ACGGGTGTCC CTAGGCGTGA CCACGCTGCT
Sa1SC_  GATCAGAGCG CCATCCCGGC ACGGGTGTCC CTAGGCGTGA CCACGCTGCT
Sa2_    GATCAGAGAG CCATCACGGC ACGGACGTGC CTGGTGGTCA CGACGGTGCT

        1351                                                   1400
Sa1LA_  CACCATGGCC ACCCAGACGT CGGGCATCAA CGCCTCCCTG CCCCCCGTGT
Sa1LC_  CACCATGGCC ACCCAGACGT CGGGCATCAA CGCCTCCCTG CCCCCCGTGT
Sa1SA_  CACCATGGCC ACCCAGACGT CGGGCATCAA CGCCTCCCTG CCCCCCGTGT
Sa1SC_  CACCATGGCC ACCCAGACGT CGGGCATCAA CGCCTCCCTG CCCCCCGTGT
Sa2_    CACCATCACC ATCCAGACCT CGGGCGTCAG AAAGTCGCTG CCCGTCGTCA
```

FIG. 1D

```
        1401                                                1450
Sa1LA_  CCTATACCAA AGCCATCGAC GTGTGGACTG GCGTGTGCCT CACTTTCGTG
Sa1LC_  CCTATACCAA AGCCATCGAC GTGTGGACTG GCGTGTGCCT CACTTTCGTG
Sa1SA_  CCTATACCAA AGCCATCGAC GTGTGGACTG GCGTGTGCCT CACTTTCGTG
Sa1SC_  CCTATACCAA AGCCATCGAC GTGTGGACTG GCGTGTGCCT CACTTTCGTG
Sa2_    ACTACGTCAT GGCCGTCGAG GTGTGGCTCG GGATGTGCGT CTCGTTCGTG

        1451                                                1500
Sa1LA_  TTCGGCGCGT TGCTCGAGTT CGCGCTCGTC AACTACGCGA GCCGCTCGGA
Sa1LC_  TTCGGCGCGT TGCTCGAGTT CGCGCTCGTC AACTACGCGA GCCGCTCGGA
Sa1SA_  TTCGGCGCGT TGCTCGAGTT CGCGCTCGTC AACTACGCGA GCCGCTCGGA
Sa1SC_  TTCGGCGCGT TGCTCGAGTT CGCGCTCGTC AACTACGCGA GCCGCTCGGA
Sa2_    TTCGGCGCAC TGCTGCAGCT GGCGCTGGTC AACTACCTGG CCCGCAAAGA

        1501                                                1550
Sa1LA_  CATGCACCGC GAGAACATGA AGAAGCAGCG CCGCCAGGTA GAGCTGGAGC
Sa1LC_  CATGCACCGC GAGAACATGA AGAAGCAGCG CCGCCAGGTA GAGCTGGAGC
Sa1SA_  CATGCACCGC GAGAACATGA AGAAGCAGCG CCGCCAGGTA GAGCTGGAGC
Sa1SC_  CATGCACCGC GAGAACATGA AGAAGCAGCG CCGCCAGGTA GAGCTGGAGC
Sa2_    GGCGTGCCGA GGCGCCGCCA AGCGGCACAA CCGCCTCGTC GGCCCGGAGC

        1551                                                1600
Sa1LA_  ACGCCGCGCA GCTCGAGGCG GCCGCTGACC TGCTCGTGGA GGACGGCAGC
Sa1LC_  ACGCCGCGCA GCTCGAGGCG GCCGCTGACC TGCTCGTGGA GGACGGCAGC
Sa1SA_  ACGCCGCGCA GCTCGAGGCG GCCGCTGACC TGCTCGTGGA GGACGGCAGC
Sa1SC_  ACGCCGCGCA GCTCGAGGCG GCCGCTGACC TGCTCGTGGA GGACGGCAGC
Sa2_    ACTCTGCACA GCTGGAGGAG ATCAGCGAGG CTCTCGTCGA GGACGGCAGC

        1601                                                1650
Sa1LA_  ACCACCTTTG CCATGAAGCC GTTGGTGGGA CACCCGGGCG GTCCGGCGGC
Sa1LC_  ACCACCTTTG CCATGAAGCC GTTGGTGGGA CACCCGGGCG GTCCGGCGGC
Sa1SA_  ACCACCTTTG CCATGAAGCC GTTGGTGGGA CACCCGGGCG GTCCGGCGGC
Sa1SC_  ACCACCTTTG CCATGAAGCC GTTGGTGGGA CACCCGGGCG GTCCGGCGGC
Sa2_    GCGGCATTCG CTATGAAGCT GCTGGAGGAG CAGTCAAACA GCCCCACGGC

        1651                                                1700
Sa1LA_  CGC..AGCGC CCGGCCTCGC AGGCCTGGAC AAGGTGCGCC AGTGCGAGAT
Sa1LC_  CGC..AGCGC CCGGCCTCGC AGGCCTGGAC AAGGTGCGCC AGTGCGAGAT
Sa1SA_  CGC..AGCGC CCGGCCTCGC AGGCCTGGAC AAGGTGCGCC AGTGCGAGAT
Sa1SC_  CGC..AGCGC CCGGCCTCGC AGGCCTGGAC AAGGTGCGCC AGTGCGAGAT
Sa2_    TGACAAGGAG GCGGCGGCCC AGGGCGG... AAGGTGCTC. ..........

        1701                                                1750
Sa1LA_  CCACATGCAG CCCAAGCGCG AAAACTGCTG CCGCACCTGG CTCTCCAAGT
Sa1LC_  CCACATGCAG CCCAAGCGCG AAAACTGCTG CCGCACCTGG CTCTCCAAGT
Sa1SA_  CCACATGCAG CCCAAGCGCG AAAACTGCTG CCGCACCTGG CTCTCCAAGT
Sa1SC_  CCACATGCAG CCCAAGCGCG AAAACTGCTG CCGCACCTGG CTCTCCAAGT
Sa2_    .........G CCGCGGC... ...AGTGGTG GCGCTCCTGG ATGGCCAGCT
```

FIG. 1E

```
        1751                                                   1800
Sa1LA_  TCCCCACGCG CTCCAAGCGC ATCGACGTCA TCTCGCGCAT CACCTTCCCG
Sa1LC_  TCCCCACGCG CTCCAAGCGC ATCGACGTCA TCTCGCGCAT CACCTTCCCG
Sa1SA_  TCCCCACGCG CTCCAAGCGC ATCGACGTCA TCTCGCGCAT CACCTTCCCG
Sa1SC_  TCCCCACGCG CTCCAAGCGC ATCGACGTCA TCTCGCGCAT CACCTTCCCG
Sa2_    TCCCCACGGG CTCGCAGCGC GCCGATGCCG CATCGCGCGT CCTCTTCCCT

        1801                                                   1850
Sa1LA_  CTCGTCTTCG CGCTCTTCAA CCTCGTCTAC TGGTCCACCT ACCTGTTCCG
Sa1LC_  CTCGTCTTCG CGCTCTTCAA CCTCGTCTAC TGGTCCACCT ACCTGTTCCG
Sa1SA_  CTCGTCTTCG CGCTCTTCAA CCTCGTCTAC TGGTCCACCT ACCTGTTCCG
Sa1SC_  CTCGTCTTCG CGCTCTTCAA CCTCGTCTAC TGGTCCACCT ACCTGTTCCG
Sa2_    CTCGCCTTCT CCCTCTTCTG CCTCGCCTAC TGGTGTGTCA ACGCCTCCGG

        1851                                                   1900
Sa1LA_  CGAGGACGAA CGCGAGTGAG CCGCCAGCCG CC....ATCG CAGCAGCAGC
Sa1LC_  CGAGGACGAC CGCGAGTGAG CCGCCAGCCG CC....ATCG CAGCAGCAGC
Sa1SA_  CGAGGACGAA CGCGAGTGAG CCGCCAGCCG CC....ATCG CAGCAGCAGC
Sa1SC_  CGAGGACGAC CGCGAGTGAG CCGCCAGCCG CC....ATCG CAGCAGCAGC
Sa2_    ATAACAGCAA CACCAGTTGC TCGGCAGTGT CCTACGATGG TGGTGGAAGT

        1901                                                   1950
Sa1LA_  CA.GCT.(SEQ ID NO:1). .......... .......... ..........
Sa1LC_  CA.GCT.(SEQ ID NO:3). .......... .......... ..........
Sa1SA_  CAAGCTACGT GGGGACGTCA TCGCC.(SEQ ID NO:5) . ..........
Sa1SC_  CAAGCTACGT GGGGACGTCA TCGCC.(SEQ ID NO:7).. ..........
Sa2_    AACCCTCCAC ACATATTTGC AGATGCACAA GCATTTATAC CTATTATAGA

        1951                                                   2000
Sa1LA_  .......... .......... .......... .......... ..........
Sa1LC_  .......... .......... .......... .......... ..........
Sa1SA_  .......... .......... .......... .......... ..........
Sa1SC_  .......... .......... .......... .......... ..........
Sa2_    ATGAAAAATA AGTATTAAAG TACTGTATAA TTCTCTATTC ATCATTACTC
        (SEQ ID NO:9)
```

FIG. 1F

```
      1                                                       50
1LA_  MMSDLCKTPW WL...CALLL LAANVPDAWC TQQKMNFREK EKQVLDQILG
1LC_  MMSDLCKTPW WL...CALLL LAANVPDAWC TQQKMNFREK EKQVLDQILG
1SA_  MMSDLCKTPW WL...CALLL LAANVPDAWC TQQKMNFREK EKQVLDQILG
1SC_  MMSDLCKTPW WL...CALLL LAANVPDAWC TQQKMNFREK EKQVLDQILG
2_    ...MLSATPS KLRRFCALVL LVVNLSKVTC SDQKTNIREA ERQVMEHVLS

      51                                                     100
1LA_  PGRYDARIRP SGINGTADNP TIVKVNIFLR SISKIDDYKM MFRCAAPLAC
1LC_  PGRYDARIRP SGINGTADNP TIVKVNIFLR SISKIDDYKM MFRCAAPLAC
1SA_  PGRYDARIRP SGINGTADNP TIVKVNIFLR SISKIDDYKM ..........
1SC_  PGRYDARIRP SGINGTADNP TIVKVNIFLR SISKIDDYKM ..........
2_    PSRYDARLRP PGYNGTES.P TVVKVNIFVR SISRVDDQHM ..........

      101                                                    150
1LA_  RPDPARRPRP SVMCFVTRVL NRSQAHRPGR QSGAACATPN KEYSVQLTFR
1LC_  RPDPARRPRP SVMCFVTRVL NRSQAHRPGR QSGAACATPN KEYSVQLTFR
1SA_  .......... .......... .......... .......... .EYSVQLTFR
1SC_  .......... .......... .......... .......... .EYSVQLTFR
2_    .......... .......... .......... .......... .EYDAQLTFR

      151                                                    200
1LA_  EQWMDERLKF NDFKGKIKYL TLTDANRVWM PDLFFSNEKE GHFHNIIMPN
1LC_  EQWMDERLKF NDFKGKIKYL TLTDANRVWM PDLFFSNEKE GHFHNIIMPN
1SA_  EQWMDERLKF NDFKGKIKYL TLTDANRVWM PDLFFSNEKE GHFHNIIMPN
1SC_  EQWMDERLKF NDFKGKIKYL TLTDANRVWM PDLFFSNEKE GHFHNIIMPN
2_    EQWFDDRLKF DDFGGKIKYL TLTDPSRIWM PDLFFSNEKK AHFHDVVMPN

      201                                                    250
1LA_  VYIRIFPYGS VLYSIRISLT LSCPMNLKLY PLDRQVCSLR MASYGWTTDD
1LC_  VYIRIFPYGS VLYSIRISLT LSCPMNLKLY PLDRQVCSLR MASYGWTTDD
1SA_  VYIRIFPYGS VLYSIRISLT LSCPMNLKLY PLDRQVCSLR MASYGWTTDD
1SC_  VYIRIFPYGS VLYSIRISLT LSCPMNLKLY PLDRQVCSLR MASYGWTTDD
2_    VYVRIFPLGS VLYSTRISMT LSCPMDLRLY PHDRQVCSIR MASYGWTTED

      251                                                    300
1LA_  LVFLWKDGDP VQVVKNLHLP RFTLEKFLTD YCNSKTNTGE YSCLKVDLLF
1LC_  LVFLWKDGDP VQVVKNLHLP RFTLEKFLTD YCNSKTNTGE YSCLKVDLLF
1SA_  LVFLWKDGDP VQVVKNLHLP RFTLEKFLTD YCNSKTNTGE YSCLKVDLLF
1SC_  LVFLWKDGDP VQVVKNLHLP RFTLEKFLTD YCNSKTNTGE YSCLKVDLLF
2_    LVFMWKDGDP VQVVKNLRLP RFTLEKFVTD YCHARTNTGE YSCLKVELVF
```

FIG.2A

```
     301                                                350
1LA_ KREFSYYLIQ IYIPCCMLVI VSWVSFWLDQ SAIPARVSLG VTTLLTMATQ
1LC_ KREFSYYLIQ IYIPCCMLVI VSWVSFWLDQ SAIPARVSLG VTTLLTMATQ
1SA_ KREFSYYLIQ IYIPCCMLVI VSWVSFWLDQ SAIPARVSLG VTTLLTMATQ
1SC_ KREFSYYLIQ IYIPCCMLVI VSWVSFWLDQ SAIPARVSLG VTTLLTMATQ
2_   KREFRYYMVH IYIPTFMLVI VSWLSFWLDQ RAITARTCLV VTTVLTITIQ

     351                                                400
1LA_ TSGINASLPP VSYTKAIDVW TGVCLTFVFG ALLEFALVNY ASRSDMHREN
1LC_ TSGINASLPP VSYTKAIDVW TGVCLTFVFG ALLEFALVNY ASRSDMHREN
1SA_ TSGINASLPP VSYTKAIDVW TGVCLTFVFG ALLEFALVNY ASRSDMHREN
1SC_ TSGINASLPP VSYTKAIDVW TGVCLTFVFG ALLEFALVNY ASRSDMHREN
2_   TSGVRKSLPV VNYVMAVEVW LGMCVSFVFG ALLQLALVNY LARKEACRGA

     401                                                450
1LA_ MKKQRRQVEL EHAAQLEAAA DLLVEDGSTT FAMKPLVGHP GGP....AAA
1LC_ MKKQRRQVEL EHAAQLEAAA DLLVEDGSTT FAMKPLVGHP GGP....AAA
1SA_ MKKQRRQVEL EHAAQLEAAA DLLVEDGSTT FAMKPLVGHP GGP....AAA
1SC_ MKKQRRQVEL EHAAQLEAAA DLLVEDGSTT FAMKPLVGHP GGP....AAA
2_   AKRHNRLVGP EHSAQLEEIS EALVEDGSAA FAMKLLEEQS NSPTADKEAA

     451                                                500
1LA_ APGLAGLDKV RQCEIHMQPK RENCCRTWLS KFPTRSKRID VISRITFPLV
1LC_ APGLAGLDKV RQCEIHMQPK RENCCRTWLS KFPTRSKRID VISRITFPLV
1SA_ APGLAGLDKV RQCEIHMQPK RENCCRTWLS KFPTRSKRID VISRITFPLV
1SC_ APGLAGLDKV RQCEIHMQPK RENCCRTWLS KFPTRSKRID VISRITFPLV
2_   AQG..GRCSP RQ........ ...WWRSWMA SFPTGSQRAD AASRVLFPLA

     501              520
1LA_ FALFNLVYWS TYLFREDERE (SEQ ID NO:2)
1LC_ FALFNLVYWS TYLFREDDRE (SEQ ID NO:4)
1SA_ FALFNLVYWS TYLFREDERE (SEQ ID NO:6)
1SC_ FALFNLVYWS TYLFREDDRE (SEQ ID NO:8)
2_   FSLFCLAYWC VNASG..... (SEQ ID NO:10)
```

FIG.2B

SEQUENCE LISTING

```
<160> NUMBER OF SEQ ID NOS: 13

<210> SEQ ID NO 1
<211> LENGTH: 1879
<212> TYPE: DNA
<213> ORGANISM: Schistocerca americana

<400> SEQUENCE: 1

gccgcacgtg ccgcacgcct cgccacgccg caccgcaggt ctcttcgccc atggaggagc     60

tcgtgcgact ggagtgagct tgtggcttac ggctctatcc gaggaaccat aagcaagtca    120

ccggcagttg agggttaact ggtaatgcgg gcgcgggtcg aggccagcag agaccgccgc    180

gtgccgcccg cggactcgca ctgccccccg gacgcgccgc cccggccgcc agccgcgcgc    240

tcgccctgct cccaccgcct ctgaagttcg agggacagct cagcctcagc atccctacag    300

gaaccatgat gagcgacctc tgcaagacgc cgtggtggct ttgtgcgctg ctgttgctgg    360

ccgccaacgt gccagatgcc tggtgcacgc agcagaagat gaacttccgc gagaaggaga    420

aacaggtgct ggaccagatc ctggggccag gtcgctacga cgcgcgcatc cggccgtcgg    480

ggatcaacgg cacagcggac aaccccacca tagtgaaagt gaacatcttc cttcgctcta    540

tcagcaaaat agacgattat aaaatgatgt tccgctgcgc tgccccgctt gcatgccgcc    600

cggaccccgc acgccgccct cggcccagcg tcatgtgttt tgttacacgt gttctcaaca    660

ggagccaggc tcaccgaccc ggccgccaat caggcgccgc gtgtgcgact ccgaacaagg    720

aatacagcgt ccagctgaca ttcagagagc agtggatgga tgagcggctc aagttcaatg    780

acttcaaagg aaaaataaag tacctgacac tgacagacgc caacagagta tggatgccag    840

atttattttt ctctaacgaa aaggaaggac attttcataa cattatcatg cccaacgttt    900

atatacgtat ttttccttat ggatcggtgc tctacagtat cagaatctct ctgacsctct    960

cctgcccgat gaacctgaag ctgtacccgc tcgacaggca ggtctgctcg ctgaggatgg   1020

ccagctatgg ttggacgact gatgacctgg tgttcctgtg gaaagacggc gacccggtgc   1080

aggtggtcaa gaacctgcac ctgccgcgct tcacgctaga gaagttcctt accgactact   1140

gcaacagcaa aactaacaca ggagagtaca gctgcttgaa ggtggacctg ctgttcaagc   1200

gcgagttcag ctactacctg atccagatct acatcccgtg ctgcatgctg gtgatagtgt   1260
```

-continued

```
cgtgggtgtc cttctggctc gatcagagcg ccatcccggc acgggtgtcc ctaggcgtga   1320

ccacgctgct caccatggcc acccagacgt cgggcatcaa cgcctccctg ccccccgtgt   1380

cctataccaa agccatcgac gtgtggactg gcgtgtgcct cactttcgtg ttcggcgcgt   1440

tgctcgagtt cgcgctcgtc aactacgcga gccgctcgga catgcaccgc gagaacatga   1500

agaagcagcg ccgccaggta gagctggagc acgccgcgca gctcgaggcg gccgctgacc   1560

tgctcgtgga ggacggcagc accacctttg ccatgaagcc gttggtggga cacccgggcg   1620

gtccggcggc cgcagcgccc ggcctcgcag gcctggacaa ggtgcgccag tgcgagatcc   1680

acatgcagcc caagcgcgaa aactgctgcc gcacctggct ctccaagttc cccacgcgct   1740

ccaagcgcat cgacgtcatc tcgcgcatca ccttcccgct cgtcttcgcg ctcttcaacc   1800

tcgtctactg gtccacctac ctgttccgcg aggacgaacg cgagtgagcc gccagccgcc   1860

atcgcagcag cagccagct                                                1879


<210> SEQ ID NO 2
<211> LENGTH: 513
<212> TYPE: PRT
<213> ORGANISM: Schistocerca americana

<400> SEQUENCE: 2

Met Met Ser Asp Leu Cys Lys Thr Pro Trp Trp Leu Cys Ala Leu Leu
 1               5                  10                  15

Leu Leu Ala Ala Asn Val Pro Asp Ala Trp Cys Thr Gln Gln Lys Met
            20                  25                  30

Asn Phe Arg Glu Lys Glu Lys Gln Val Leu Asp Gln Ile Leu Gly Pro
        35                  40                  45

Gly Arg Tyr Asp Ala Arg Ile Arg Pro Ser Gly Ile Asn Gly Thr Ala
    50                  55                  60

Asp Asn Pro Thr Ile Val Lys Val Asn Ile Phe Leu Arg Ser Ile Ser
65                  70                  75                  80

Lys Ile Asp Asp Tyr Lys Met Met Phe Arg Cys Ala Ala Pro Leu Ala
                85                  90                  95

Cys Arg Pro Asp Pro Ala Arg Arg Pro Arg Pro Ser Val Met Cys Phe
            100                 105                 110

Val Thr Arg Val Leu Asn Arg Ser Gln Ala His Arg Pro Gly Arg Gln
        115                 120                 125

Ser Gly Ala Ala Cys Ala Thr Pro Asn Lys Glu Tyr Ser Val Gln Leu
    130                 135                 140

Thr Phe Arg Glu Gln Trp Met Asp Glu Arg Leu Lys Phe Asn Asp Phe
145                 150                 155                 160

Lys Gly Lys Ile Lys Tyr Leu Thr Leu Thr Asp Ala Asn Arg Val Trp
                165                 170                 175

Met Pro Asp Leu Phe Phe Ser Asn Glu Lys Glu Gly His Phe His Asn
            180                 185                 190

Ile Ile Met Pro Asn Val Tyr Ile Arg Ile Phe Pro Tyr Gly Ser Val
        195                 200                 205

Leu Tyr Ser Ile Arg Ile Ser Leu Thr Leu Ser Cys Pro Met Asn Leu
    210                 215                 220

Lys Leu Tyr Pro Leu Asp Arg Gln Val Cys Ser Leu Arg Met Ala Ser
225                 230                 235                 240

Tyr Gly Trp Thr Thr Asp Asp Leu Val Phe Leu Trp Lys Asp Gly Asp
                245                 250                 255
```

-continued

```
Pro Val Gln Val Val Lys Asn Leu His Leu Pro Arg Phe Thr Leu Glu
            260                 265                 270

Lys Phe Leu Thr Asp Tyr Cys Asn Ser Lys Thr Asn Thr Gly Glu Tyr
        275                 280                 285

Ser Cys Leu Lys Val Asp Leu Leu Phe Lys Arg Glu Phe Ser Tyr Tyr
    290                 295                 300

Leu Ile Gln Ile Tyr Ile Pro Cys Cys Met Leu Val Ile Val Ser Trp
305                 310                 315                 320

Val Ser Phe Trp Leu Asp Gln Ser Ala Ile Pro Ala Arg Val Ser Leu
                325                 330                 335

Gly Val Thr Thr Leu Leu Thr Met Ala Thr Gln Thr Ser Gly Ile Asn
            340                 345                 350

Ala Ser Leu Pro Pro Val Ser Tyr Thr Lys Ala Ile Asp Val Trp Thr
        355                 360                 365

Gly Val Cys Leu Thr Phe Val Phe Gly Ala Leu Leu Glu Phe Ala Leu
    370                 375                 380

Val Asn Tyr Ala Ser Arg Ser Asp Met His Arg Glu Asn Met Lys Lys
385                 390                 395                 400

Gln Arg Arg Gln Val Glu Leu Glu His Ala Ala Gln Leu Glu Ala Ala
                405                 410                 415

Ala Asp Leu Leu Val Glu Asp Gly Ser Thr Thr Phe Ala Met Lys Pro
            420                 425                 430

Leu Val Gly His Pro Gly Gly Pro Ala Ala Ala Ala Pro Gly Leu Ala
        435                 440                 445

Gly Leu Asp Lys Val Arg Gln Cys Glu Ile His Met Gln Pro Lys Arg
    450                 455                 460

Glu Asn Cys Cys Arg Thr Trp Leu Ser Lys Phe Pro Thr Arg Ser Lys
465                 470                 475                 480

Arg Ile Asp Val Ile Ser Arg Ile Thr Phe Pro Leu Val Phe Ala Leu
                485                 490                 495

Phe Asn Leu Val Tyr Trp Ser Thr Tyr Leu Phe Arg Glu Asp Glu Arg
            500                 505                 510

Glu
```

<210> SEQ ID NO 3
<211> LENGTH: 1879
<212> TYPE: DNA
<213> ORGANISM: Schistocerca americana

<400> SEQUENCE: 3

```
gccgcacgtg ccgcacgcct cgccacgccg caccgcaggt ctcttcgccc atggaggagc     60

tcgtgcgact ggagtgagct tgtggcttac ggctctatcc gaggaaccat aagcaagtca    120

ccggcagttg agggttaact ggtaatgcgg gcgcgggtcg aggccagcag agaccgccgc    180

gtgccgcccg cggactcgca ctgccccccg gacgcgccgc cccggccgcc agccgcgcgc    240

tcgccctgct cccaccgcct ctgaagttcg agggacagct cagcctcagc atccctacag    300

gaaccatgat gagcgacctc tgcaagacgc cgtggtggct ttgtgcgctg ctgttgctgg    360

ccgccaacgt gccagatgcc tggtgcacgc agcagaagat gaacttccgc gagaaggaga    420

aacaggtgct ggaccagatc ctggggccag gtcgctacga cgcgcgcatc cggccgtcgg    480

ggatcaacgg cacagcggac aaccccacca tagtgaaagt gaacatcttc cttcgctcta    540

tcagcaaaat agacgattat aaaatgatgt tccgctgcgc tgccccgctt gcatgccgcc    600

cggaccccgc acgccgccct cggcccagcg tcatgtgttt tgttacacgt gttctcaaca    660
```

-continued

```
ggagccaggc tcaccgaccc ggccgccaat caggcgccgc gtgtgcgact ccgaacaagg    720
aatacagcgt ccagctgaca ttcagagagc agtggatgga tgagcggctc aagttcaatg    780
acttcaaagg aaaaataaag tacctgacac tgacagacgc caacagagta tggatgccag    840
atttattttt ctctaacgaa aaggaaggac attttcataa cattatcatg cccaacgttt    900
atatacgtat ttttccttat ggatcggtgc tctacagtat cagaatctct ctgacsctct    960
cctgcccgat gaacctgaag ctgtacccgc tcgacaggca ggtctgctcg ctgaggatgg   1020
ccagctatgg ttggacgact gatgacctgg tgttcctgtg gaaagacggc gacccggtgc   1080
aggtggtcaa gaacctgcac ctgccgcgct tcacgctaga gaagttcctt accgactact   1140
gcaacagcaa aactaacaca ggagagtaca gctgcttgaa ggtggacctg ctgttcaagc   1200
gcgagttcag ctactacctg atccagatct acatcccgtg ctgcatgctg gtgatagtgt   1260
cgtgggtgtc cttctggctc gatcagagcg ccatcccggc acgggtgtcc ctaggcgtga   1320
ccacgctgct caccatggcc acccagacgt cgggcatcaa cgcctccctg ccccccgtgt   1380
cctataccaa agccatcgac gtgtggactg gcgtgtgcct cactttcgtg ttcggcgcgt   1440
tgctcgagtt cgcgctcgtc aactacgcga gccgctcgga catgcaccgc gagaacatga   1500
agaagcagcg ccgccaggta gagctggagc acgccgcgca gctcgaggcg gccgctgacc   1560
tgctcgtgga ggacggcagc accacctttg ccatgaagcc gttggtggga cacccgggcg   1620
gtccggcggc cgcagcgccc ggcctcgcag gcctggacaa ggtgcgccag tgcgagatcc   1680
acatgcagcc caagcgcgaa aactgctgcc gcacctggct ctccaagttc ccacgcgct    1740
ccaagcgcat cgacgtcatc tcgcgcatca ccttcccgct cgtcttcgcg ctcttcaacc   1800
tcgtctactg gtccacctac ctgttccgcg aggacgaccg cgagtgagcc gccagccgcc   1860
atcgcagcag cagccagct                                                1879
```

<210> SEQ ID NO 4
<211> LENGTH: 513
<212> TYPE: PRT
<213> ORGANISM: Schistocerca americana

<400> SEQUENCE: 4

```
Met Met Ser Asp Leu Cys Lys Thr Pro Trp Trp Leu Cys Ala Leu Leu
 1               5                  10                  15

Leu Leu Ala Ala Asn Val Pro Asp Ala Trp Cys Thr Gln Gln Lys Met
            20                  25                  30

Asn Phe Arg Glu Lys Glu Lys Gln Val Leu Asp Gln Ile Leu Gly Pro
        35                  40                  45

Gly Arg Tyr Asp Ala Arg Ile Arg Pro Ser Gly Ile Asn Gly Thr Ala
    50                  55                  60

Asp Asn Pro Thr Ile Val Lys Val Asn Ile Phe Leu Arg Ser Ile Ser
65                  70                  75                  80

Lys Ile Asp Asp Tyr Lys Met Met Phe Arg Cys Ala Ala Pro Leu Ala
                85                  90                  95

Cys Arg Pro Asp Pro Ala Arg Arg Pro Arg Pro Ser Val Met Cys Phe
            100                 105                 110

Val Thr Arg Val Leu Asn Arg Ser Gln Ala His Arg Pro Gly Arg Gln
        115                 120                 125

Ser Gly Ala Ala Cys Ala Thr Pro Asn Lys Glu Tyr Ser Val Gln Leu
    130                 135                 140

Thr Phe Arg Glu Gln Trp Met Asp Glu Arg Leu Lys Phe Asn Asp Phe
```

-continued

```
145                 150                 155                 160

Lys Gly Lys Ile Lys Tyr Leu Thr Leu Thr Asp Ala Asn Arg Val Trp
                165                 170                 175

Met Pro Asp Leu Phe Phe Ser Asn Glu Lys Glu Gly His Phe His Asn
            180                 185                 190

Ile Ile Met Pro Asn Val Tyr Ile Arg Ile Phe Pro Tyr Gly Ser Val
        195                 200                 205

Leu Tyr Ser Ile Arg Ile Ser Leu Thr Leu Ser Cys Pro Met Asn Leu
    210                 215                 220

Lys Leu Tyr Pro Leu Asp Arg Gln Val Cys Ser Leu Arg Met Ala Ser
225                 230                 235                 240

Tyr Gly Trp Thr Thr Asp Asp Leu Val Phe Leu Trp Lys Asp Gly Asp
                245                 250                 255

Pro Val Gln Val Val Lys Asn Leu His Leu Pro Arg Phe Thr Leu Glu
            260                 265                 270

Lys Phe Leu Thr Asp Tyr Cys Asn Ser Lys Thr Asn Thr Gly Glu Tyr
        275                 280                 285

Ser Cys Leu Lys Val Asp Leu Leu Phe Lys Arg Glu Phe Ser Tyr Tyr
    290                 295                 300

Leu Ile Gln Ile Tyr Ile Pro Cys Cys Met Leu Val Ile Val Ser Trp
305                 310                 315                 320

Val Ser Phe Trp Leu Asp Gln Ser Ala Ile Pro Ala Arg Val Ser Leu
                325                 330                 335

Gly Val Thr Thr Leu Leu Thr Met Ala Thr Gln Thr Ser Gly Ile Asn
            340                 345                 350

Ala Ser Leu Pro Pro Val Ser Tyr Thr Lys Ala Ile Asp Val Trp Thr
        355                 360                 365

Gly Val Cys Leu Thr Phe Val Phe Gly Ala Leu Leu Glu Phe Ala Leu
    370                 375                 380

Val Asn Tyr Ala Ser Arg Ser Asp Met His Arg Glu Asn Met Lys Lys
385                 390                 395                 400

Gln Arg Arg Gln Val Glu Leu Glu His Ala Ala Gln Leu Glu Ala Ala
                405                 410                 415

Ala Asp Leu Leu Val Glu Asp Gly Ser Thr Thr Phe Ala Met Lys Pro
            420                 425                 430

Leu Val Gly His Pro Gly Gly Pro Ala Ala Ala Ala Pro Gly Leu Ala
        435                 440                 445

Gly Leu Asp Lys Val Arg Gln Cys Glu Ile His Met Gln Pro Lys Arg
    450                 455                 460

Glu Asn Cys Cys Arg Thr Trp Leu Ser Lys Phe Pro Thr Arg Ser Lys
465                 470                 475                 480

Arg Ile Asp Val Ile Ser Arg Ile Thr Phe Pro Leu Val Phe Ala Leu
                485                 490                 495

Phe Asn Leu Val Tyr Trp Ser Thr Tyr Leu Phe Arg Glu Asp Asp Arg
            500                 505                 510

Glu

<210> SEQ ID NO 5
<211> LENGTH: 1766
<212> TYPE: DNA
<213> ORGANISM: Schistocerca americana

<400> SEQUENCE: 5

agcagtggcg cgactaccgc cgcacgtgcc gcacgcctcg ccacgccgca ccgcaggtct     60
```

-continued

```
cttcgctcat ggaggagctc gtgcgactgg agtgagcgtg tggcttacgg ctctatccga    120
ggaaccataa gcaacagtca ccggcagttg agggttaact ggtaatgcgg gcgcgggtcg    180
aggccagcag agaccgccgc gtgccgcccg cggactcgca ctgccccccg gacgcgccgc    240
cccggccgcc agccgcgcgc tcgccctgct cccgccgcct ctgaagtcca agggttagct    300
cagcctcagc atccctgcag gaaccatgat gagcgacctc tgcaagacgc cgtggtggct    360
ttgtgcgctg ctgttgctgg ccgccaacgt gccagatgcc tggtgcacgc agcagaagat    420
gaacttccgc gagaaggaga aacaggtgct ggaccagatc ctggggccag gtcgctacga    480
cgctcgcatc cggccgtcgg ggatcaacgg cacagcggac aaccccacca tagtgaaagt    540
gaacatcttc cttcgctcta tcagcaaaat agacgattat aaaatggaat acagcgtcca    600
gctgacattc agagagcagt ggatggatga gcggctcaag ttcaatgact tcaaaggaaa    660
aataaagtac ctgacactga cagacgccaa cagagtatgg atgccagatt tatttttctc    720
taacgaaaag gaaggacatt ttcataacat tatcatgccc aacgtttata tacgtatttt    780
tccttatgga tcggtgctct acagtatcag aatctctctg acgctctcct gcccgatgaa    840
cctgaagctg tacccgctcg acaggcaggt ctgctcgctg aggatggcca gctatggttg    900
gacgactgat gacctggtgt tcctgtggaa agacggcgac ccggtgcagg tggtcaagaa    960
cctgcacctg ccgcgcttca cgctagagaa gttccttacc gactactgca acagcaaaac   1020
caacacagga gagtacagct gcttgaaggt ggacctgctg ttcaagcgcg agttcagcta   1080
ctacctgatc cagatctaca tcccgtgctg catgctggtg atagtgtcgt gggtgtcctt   1140
ctggctcgat cagagcgcca tcccggcacg ggtgtcccta ggcgtgacca cgctgctcac   1200
catggccacc cagacgtcgg gcatcaacgc ctccctgccc cccgtgtcct ataccaaagc   1260
catcgacgtg tggactggcg tgtgcctcac tttcgtgttc ggcgcgttgc tcgagttcgc   1320
gctcgtcaac tacgcgagcc gctcggacat gcaccgcgag aacatgaaga agcagcgccg   1380
ccaggtagag ctggagcacg ccgcgcagct cgaggcggcc gctgacctgc tcgtggagga   1440
cggcagcacc acctttgcca tgaagccgtt ggtgggacac ccgggcggtc cggcggccgc   1500
agcgcccggc ctcgcaggcc tggacaaggt gcgccagtgc gagatccaca tgcagcccaa   1560
gcgcgaaaac tgctgccgca cctggctctc caagttcccc acgcgctcca agcgcatcga   1620
cgtcatctcg cgcatcacct tcccgctcgt cttcgcgctc ttcaacctcg tctactggtc   1680
cacctacctg ttccgcgagg acgaacgcga gtgagccgcc agccgccatc gcagcagcag   1740
ccaagctacg tggggacgtc atcgcc                                        1766
```

<210> SEQ ID NO 6
<211> LENGTH: 462
<212> TYPE: PRT
<213> ORGANISM: Schistocerca americana

<400> SEQUENCE: 6

```
Met Met Ser Asp Leu Cys Lys Thr Pro Trp Trp Leu Cys Ala Leu Leu
 1               5                  10                  15

Leu Leu Ala Ala Asn Val Pro Asp Ala Trp Cys Thr Gln Gln Lys Met
            20                  25                  30

Asn Phe Arg Glu Lys Glu Lys Gln Val Leu Asp Gln Ile Leu Gly Pro
        35                  40                  45

Gly Arg Tyr Asp Ala Arg Ile Arg Pro Ser Gly Ile Asn Gly Thr Ala
    50                  55                  60
```

-continued

```
Asp Asn Pro Thr Ile Val Lys Val Asn Ile Phe Leu Arg Ser Ile Ser
65                  70                  75                  80

Lys Ile Asp Asp Tyr Lys Met Glu Tyr Ser Val Gln Leu Thr Phe Arg
                85                  90                  95

Glu Gln Trp Met Asp Glu Arg Leu Lys Phe Asn Asp Phe Lys Gly Lys
            100                 105                 110

Ile Lys Tyr Leu Thr Leu Thr Asp Ala Asn Arg Val Trp Met Pro Asp
        115                 120                 125

Leu Phe Phe Ser Asn Glu Lys Glu Gly His Phe His Asn Ile Ile Met
    130                 135                 140

Pro Asn Val Tyr Ile Arg Ile Phe Pro Tyr Gly Ser Val Leu Tyr Ser
145                 150                 155                 160

Ile Arg Ile Ser Leu Thr Leu Ser Cys Pro Met Asn Leu Lys Leu Tyr
                165                 170                 175

Pro Leu Asp Arg Gln Val Cys Ser Leu Arg Met Ala Ser Tyr Gly Trp
            180                 185                 190

Thr Thr Asp Asp Leu Val Phe Leu Trp Lys Asp Gly Asp Pro Val Gln
        195                 200                 205

Val Val Lys Asn Leu His Leu Pro Arg Phe Thr Leu Glu Lys Phe Leu
    210                 215                 220

Thr Asp Tyr Cys Asn Ser Lys Thr Asn Thr Gly Glu Tyr Ser Cys Leu
225                 230                 235                 240

Lys Val Asp Leu Leu Phe Lys Arg Glu Phe Ser Tyr Tyr Leu Ile Gln
                245                 250                 255

Ile Tyr Ile Pro Cys Cys Met Leu Val Ile Val Ser Trp Val Ser Phe
            260                 265                 270

Trp Leu Asp Gln Ser Ala Ile Pro Ala Arg Val Ser Leu Gly Val Thr
        275                 280                 285

Thr Leu Leu Thr Met Ala Thr Gln Thr Ser Gly Ile Asn Ala Ser Leu
    290                 295                 300

Pro Pro Val Ser Tyr Thr Lys Ala Ile Asp Val Trp Thr Gly Val Cys
305                 310                 315                 320

Leu Thr Phe Val Phe Gly Ala Leu Leu Glu Phe Ala Leu Val Asn Tyr
                325                 330                 335

Ala Ser Arg Ser Asp Met His Arg Glu Asn Met Lys Lys Gln Arg Arg
            340                 345                 350

Gln Val Glu Leu Glu His Ala Ala Gln Leu Glu Ala Ala Ala Asp Leu
        355                 360                 365

Leu Val Glu Asp Gly Ser Thr Thr Phe Ala Met Lys Pro Leu Val Gly
    370                 375                 380

His Pro Gly Gly Pro Ala Ala Ala Ala Pro Gly Leu Ala Gly Leu Asp
385                 390                 395                 400

Lys Val Arg Gln Cys Glu Ile His Met Gln Pro Lys Arg Glu Asn Cys
                405                 410                 415

Cys Arg Thr Trp Leu Ser Lys Phe Pro Thr Arg Ser Lys Arg Ile Asp
            420                 425                 430

Val Ile Ser Arg Ile Thr Phe Pro Leu Val Phe Ala Leu Phe Asn Leu
        435                 440                 445

Val Tyr Trp Ser Thr Tyr Leu Phe Arg Glu Asp Glu Arg Glu
    450                 455                 460
```

<210> SEQ ID NO 7
<211> LENGTH: 1766
<212> TYPE: DNA

-continued

<213> ORGANISM: Schistocerca americana

<400> SEQUENCE: 7
agcagtggcg cgactaccgc cgcacgtgcc gcacgcctcg ccacgccgca ccgcaggtct 60
cttcgctcat ggaggagctc gtgcgactgg agtgagcgtg tggcttacgg ctctatccga 120
ggaaccataa gcaacagtca ccggcagttg agggttaact ggtaatgcgg gcgcgggtcg 180
aggccagcag agaccgccgc gtgccgcccg cggactcgca ctgccccccg gacgcgccgc 240
cccggccgcc agccgcgcgc tcgccctgct cccgccgcct ctgaagtcca agggttagct 300
cagcctcagc atccctgcag gaaccatgat gagcgacctc tgcaagacgc cgtggtggct 360
ttgtgcgctg ctgttgctgg ccgccaacgt gccagatgcc tggtgcacgc agcagaagat 420
gaacttccgc gagaaggaga aacaggtgct ggaccagatc ctggggccag gtcgctacga 480
cgctcgcatc cggccgtcgg ggatcaacgg cacagcggac aaccccacca tagtgaaagt 540
gaacatcttc cttcgctcta tcagcaaaat agacgattat aaaatggaat acagcgtcca 600
gctgacattc agagagcagt ggatggatga gcggctcaag ttcaatgact tcaaaggaaa 660
aataaagtac ctgacactga cagacgccaa cagagtatgg atgccagatt tatttttctc 720
taacgaaaag gaaggacatt ttcataacat tatcatgccc aacgtttata tacgtatttt 780
tccttatgga tcggtgctct acagtatcag aatctctctg acgctctcct gcccgatgaa 840
cctgaagctg tacccgctcg acaggcaggt ctgctcgctg aggatggcca gctatggttg 900
gacgactgat gacctggtgt tcctgtggaa agacggcgac ccggtgcagg tggtcaagaa 960
cctgcacctg ccgcgcttca cgctagagaa gttccttacc gactactgca acagcaaaac 1020
caacacagga gagtacagct gcttgaaggt ggacctgctg ttcaagcgcg agttcagcta 1080
ctacctgatc cagatctaca tcccgtgctg catgctggtg atagtgtcgt gggtgtcctt 1140
ctggctcgat cagagcgcca tcccggcacg ggtgtcccta ggcgtgacca cgctgctcac 1200
catggccacc cagacgtcgg gcatcaacgc ctccctgccc cccgtgtcct ataccaaagc 1260
catcgacgtg tggactggcg tgtgcctcac tttcgtgttc ggcgcgttgc tcgagttcgc 1320
gctcgtcaac tacgcgagcc gctcggacat gcaccgcgag aacatgaaga agcagcgccg 1380
ccaggtagag ctggagcacg ccgcgcagct cgaggcggcc gctgacctgc tcgtggagga 1440
cggcagcacc acctttgcca tgaagccgtt ggtgggacac ccgggcggtc cggcggccgc 1500
agcgcccggc ctcgcaggcc tggacaaggt gcgccagtgc gagatccaca tgcagcccaa 1560
gcgcgaaaac tgctgccgca cctggctctc caagttcccc acgcgctcca agcgcatcga 1620
cgtcatctcg cgcatcacct tcccgctcgt cttcgcgctc ttcaacctcg tctactggtc 1680
cacctacctg ttccgcgagg acgaccgcga gtgagccgcc agccgccatc gcagcagcag 1740
ccaagctacg tggggacgtc atcgcc 1766

<210> SEQ ID NO 8
<211> LENGTH: 462
<212> TYPE: PRT
<213> ORGANISM: Schistocerca americana

<400> SEQUENCE: 8

Met Met Ser Asp Leu Cys Lys Thr Pro Trp Trp Leu Cys Ala Leu Leu
1 5 10 15

Leu Leu Ala Ala Asn Val Pro Asp Ala Trp Cys Thr Gln Gln Lys Met
20 25 30

Asn Phe Arg Glu Lys Glu Lys Gln Val Leu Asp Gln Ile Leu Gly Pro

-continued

```
        35                  40                  45

Gly Arg Tyr Asp Ala Arg Ile Arg Pro Ser Gly Ile Asn Gly Thr Ala
    50                  55                  60

Asp Asn Pro Thr Ile Val Lys Val Asn Ile Phe Leu Arg Ser Ile Ser
65                  70                  75                  80

Lys Ile Asp Asp Tyr Lys Met Glu Tyr Ser Val Gln Leu Thr Phe Arg
                85                  90                  95

Glu Gln Trp Met Asp Glu Arg Leu Lys Phe Asn Asp Phe Lys Gly Lys
            100                 105                 110

Ile Lys Tyr Leu Thr Leu Thr Asp Ala Asn Arg Val Trp Met Pro Asp
        115                 120                 125

Leu Phe Phe Ser Asn Glu Lys Glu Gly His Phe His Asn Ile Ile Met
    130                 135                 140

Pro Asn Val Tyr Ile Arg Ile Phe Pro Tyr Gly Ser Val Leu Tyr Ser
145                 150                 155                 160

Ile Arg Ile Ser Leu Thr Leu Ser Cys Pro Met Asn Leu Lys Leu Tyr
                165                 170                 175

Pro Leu Asp Arg Gln Val Cys Ser Leu Arg Met Ala Ser Tyr Gly Trp
            180                 185                 190

Thr Thr Asp Asp Leu Val Phe Leu Trp Lys Asp Gly Asp Pro Val Gln
        195                 200                 205

Val Val Lys Asn Leu His Leu Pro Arg Phe Thr Leu Glu Lys Phe Leu
    210                 215                 220

Thr Asp Tyr Cys Asn Ser Lys Thr Asn Thr Gly Glu Tyr Ser Cys Leu
225                 230                 235                 240

Lys Val Asp Leu Leu Phe Lys Arg Glu Phe Ser Tyr Tyr Leu Ile Gln
                245                 250                 255

Ile Tyr Ile Pro Cys Cys Met Leu Val Ile Val Ser Trp Val Ser Phe
            260                 265                 270

Trp Leu Asp Gln Ser Ala Ile Pro Ala Arg Val Ser Leu Gly Val Thr
        275                 280                 285

Thr Leu Leu Thr Met Ala Thr Gln Thr Ser Gly Ile Asn Ala Ser Leu
    290                 295                 300

Pro Pro Val Ser Tyr Thr Lys Ala Ile Asp Val Trp Thr Gly Val Cys
305                 310                 315                 320

Leu Thr Phe Val Phe Gly Ala Leu Leu Glu Phe Ala Leu Val Asn Tyr
                325                 330                 335

Ala Ser Arg Ser Asp Met His Arg Glu Asn Met Lys Lys Gln Arg Arg
            340                 345                 350

Gln Val Glu Leu Glu His Ala Ala Gln Leu Glu Ala Ala Ala Asp Leu
        355                 360                 365

Leu Val Glu Asp Gly Ser Thr Thr Phe Ala Met Lys Pro Leu Val Gly
    370                 375                 380

His Pro Gly Gly Pro Ala Ala Ala Ala Pro Gly Leu Ala Gly Leu Asp
385                 390                 395                 400

Lys Val Arg Gln Cys Glu Ile His Met Gln Pro Lys Arg Glu Asn Cys
                405                 410                 415

Cys Arg Thr Trp Leu Ser Lys Phe Pro Thr Arg Ser Lys Arg Ile Asp
            420                 425                 430

Val Ile Ser Arg Ile Thr Phe Pro Leu Val Phe Ala Leu Phe Asn Leu
        435                 440                 445

Val Tyr Trp Ser Thr Tyr Leu Phe Arg Glu Asp Asp Arg Glu
    450                 455                 460
```

-continued

<210> SEQ ID NO 9
<211> LENGTH: 2074
<212> TYPE: DNA
<213> ORGANISM: Schistocerca americana

<400> SEQUENCE: 9
ggcacgaggg cgtctcggct gtccacacac agcaggaatc atgctgagcg caacacccag 60
caagctgcgg cgattttgtg ctttggtgct gttggttgtg aatctgtcaa aagtcacatg 120
ctcggatcag aagactaaca tccgggaggc ggagaggcag gtgatggagc acgtcctgag 180
cccgagccgc tacgacgcgc ggctgcggcc cccgggatac aacggcacag agagtcccac 240
tgtggtaaaa gttaacatct ttgtacgctc catcagcaga gtagatgatc agcatatgga 300
atatgacgcg cagttgacgt tcagagagca gtggtttgac gacaggctca agtttgacga 360
ttttggaggt aaaatcaaat atctaacact gacagatccc agcagaatat ggatgccaga 420
tttatttttt agcaacgaga agaaagcaca ctttcacgat gtagtaatgc ctaatgtcta 480
tgtacgaata tttcctcttg ggtcggttct ctacagtacc agaatctcaa tgacactctc 540
gtgtcccatg gacctgaggc tgtacccaca cgatcgacag gtgtgctcca tcaggatggc 600
cagctatggt tggacgactg aagacctggt gttcatgtgg aaagacggcg acccggtgca 660
ggtggtcaag aacctgcgcc ttccacgctt cacgctagag aagttcgtta ctgattactg 720
ccacgccagg acaaacacag gcgagtacag ctgccttaaa gtggaactgg tgtttaaacg 780
cgagttccgc tactacatgg tgcacatcta cattccgact ttcatgctgg tgatagtgtc 840
gtggctatcg ttctggctgg atcagagagc catcacggca cggacgtgcc tggtggtcac 900
gacggtgctc accatcacca tccagacctc gggcgtcaga aagtcgctgc ccgtcgtcaa 960
ctacgtcatg gccgtcgagg tgtggctcgg gatgtgcgtc tcgttcgtgt tcggcgcact 1020
gctgcagctg gcgctggtca actacctggc ccgcaaagag gcgtgccgag gcgccgccaa 1080
gcggcacaac cgcctcgtcg gcccggagca ctctgcacag ctggaggaga tcagcgaggc 1140
tctcgtcgag gacggcagcg cggcattcgc tatgaagctg ctggaggagc agtcaaacag 1200
ccccacggct gacaaggagg cggcggccca gggcggaagg tgctcgccgc ggcagtggtg 1260
gcgctcctgg atggccagct tccccacggg ctcgcagcgc gccgatgccg catcgcgcgt 1320
cctcttccct ctcgccttct ccctcttctg cctcgcctac tggtgtgtca acgcctccgg 1380
ataacagcaa caccagttgc tcggcagtgt cctacgatgg tggtggaagt aaccctccac 1440
acatatttgc agatgcacaa gcatttatac ctattataga atgaaaaata agtattaaag 1500
tactgtataa ttctctattc atcattactc ttactgtatc gacattactg tttgacggca 1560
atttcgttat acgagatttg tccggaaaat acgcataaaa gttgaattat aactttattt 1620
tacaattatt caggtattac aatatggtct ccttcaaagt actcgccctg agatgcgata 1680
cactgctgtc aacgccgttt acactgttga taatattgct gaaagtcttc agttgtgatg 1740
ttgttcagtt gccgtgtcgt ttccgccttg tggcttccac atctcccaag tgccgccctc 1800
gaagcacgat tttgcatttc tggaacatga agaagtcaca tggggctaaa gcgggtgaat 1860
aaggcgggtg gtctgtcacg gtgattgagc ttcaggccaa aaactcgcgc acaacgagcg 1920
acgtgtgagc gggcgctttg tcgtgctgaa ggatccacct gccccctttt gccaactccg 1980
gtcgaactcg ggccacacga gctctgagac gtgtcagaac ttcaacgtaa aaatttccgt 2040
tcactctctg gccgggaagg acaaattcct tgtg 2074

-continued

<210> SEQ ID NO 10
<211> LENGTH: 447
<212> TYPE: PRT
<213> ORGANISM: Schistocerca americana

<400> SEQUENCE: 10

```
Met Leu Ser Ala Thr Pro Ser Lys Leu Arg Arg Phe Cys Ala Leu Val
 1               5                  10                  15

Leu Leu Val Val Asn Leu Ser Lys Val Thr Cys Ser Asp Gln Lys Thr
            20                  25                  30

Asn Ile Arg Glu Ala Glu Arg Gln Val Met Glu His Val Leu Ser Pro
        35                  40                  45

Ser Arg Tyr Asp Ala Arg Leu Arg Pro Pro Gly Tyr Asn Gly Thr Glu
    50                  55                  60

Ser Pro Thr Val Val Lys Val Asn Ile Phe Val Arg Ser Ile Ser Arg
65                  70                  75                  80

Val Asp Asp Gln His Met Glu Tyr Asp Ala Gln Leu Thr Phe Arg Glu
                85                  90                  95

Gln Trp Phe Asp Asp Arg Leu Lys Phe Asp Asp Phe Gly Gly Lys Ile
            100                 105                 110

Lys Tyr Leu Thr Leu Thr Asp Pro Ser Arg Ile Trp Met Pro Asp Leu
        115                 120                 125

Phe Phe Ser Asn Glu Lys Lys Ala His Phe His Asp Val Val Met Pro
    130                 135                 140

Asn Val Tyr Val Arg Ile Phe Pro Leu Gly Ser Val Leu Tyr Ser Thr
145                 150                 155                 160

Arg Ile Ser Met Thr Leu Ser Cys Pro Met Asp Leu Arg Leu Tyr Pro
                165                 170                 175

His Asp Arg Gln Val Cys Ser Ile Arg Met Ala Ser Tyr Gly Trp Thr
            180                 185                 190

Thr Glu Asp Leu Val Phe Met Trp Lys Asp Gly Asp Pro Val Gln Val
        195                 200                 205

Val Lys Asn Leu Arg Leu Pro Arg Phe Thr Leu Glu Lys Phe Val Thr
    210                 215                 220

Asp Tyr Cys His Ala Arg Thr Asn Thr Gly Glu Tyr Ser Cys Leu Lys
225                 230                 235                 240

Val Glu Leu Val Phe Lys Arg Glu Phe Arg Tyr Tyr Met Val His Ile
                245                 250                 255

Tyr Ile Pro Thr Phe Met Leu Val Ile Val Ser Trp Leu Ser Phe Trp
            260                 265                 270

Leu Asp Gln Arg Ala Ile Thr Ala Arg Thr Cys Leu Val Val Thr Thr
        275                 280                 285

Val Leu Thr Ile Thr Ile Gln Thr Ser Gly Val Arg Lys Ser Leu Pro
    290                 295                 300

Val Val Asn Tyr Val Met Ala Val Glu Val Trp Leu Gly Met Cys Val
305                 310                 315                 320

Ser Phe Val Phe Gly Ala Leu Leu Gln Leu Ala Leu Val Asn Tyr Leu
                325                 330                 335

Ala Arg Lys Glu Ala Cys Arg Gly Ala Ala Lys Arg His Asn Arg Leu
            340                 345                 350

Val Gly Pro Glu His Ser Ala Gln Leu Glu Glu Ile Ser Glu Ala Leu
        355                 360                 365

Val Glu Asp Gly Ser Ala Ala Phe Ala Met Lys Leu Leu Glu Glu Gln
    370                 375                 380
```

-continued

```
Ser Asn Ser Pro Thr Ala Asp Lys Glu Ala Ala Ala Gln Gly Gly Arg
385                 390                 395                 400

Cys Ser Pro Arg Gln Trp Trp Arg Ser Trp Met Ala Ser Phe Pro Thr
                405                 410                 415

Gly Ser Gln Arg Ala Asp Ala Ala Ser Arg Val Leu Phe Pro Leu Ala
            420                 425                 430

Phe Ser Leu Phe Cys Leu Ala Tyr Trp Cys Val Asn Ala Ser Gly
        435                 440                 445


<210> SEQ ID NO 11
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)...(27)
<223> OTHER INFORMATION: n = A,T,C or G

<400> SEQUENCE: 11

ggatkccnga ynynttyttn nmnamyg                                          27


<210> SEQ ID NO 12
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)...(24)
<223> OTHER INFORMATION: n = A,T,C or G

<400> SEQUENCE: 12

cnarmarngc ncmgaanayr aayg                                             24


<210> SEQ ID NO 13
<211> LENGTH: 26
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)...(26)
<223> OTHER INFORMATION: n = A,T,C or G

<400> SEQUENCE: 13

canrcnccnr kccanacrtc naynrc                                           26
```

DNA MOLECULES ENCODING L-GLUTAMATE-GATED CHLORIDE CHANNELS FROM *SCHISTOCERCA AMERICANA*

CROSS-REFERENCE TO RELATED APPLICATIONS

This application claims the benefit of U.S. Provisional Application Ser. No. 60/160,877, filed Oct. 22, 1999, under 35 U.S.C. § 119(e).

STATEMENT REGARDING FEDERALLY-SPONSORED R&D

Not Applicable

REFERENCE TO MICROFICHE APPENDIX

Not Applicable

FIELD OF THE INVENTION

The present invention relates in part to isolated nucleic acid molecules (polynucleotides) which encode *Schistocerca americana* (grasshopper) glutamate-gated chloride channels. The present invention also relates to recombinant vectors and recombinant hosts which contain a DNA fragment encoding *S. americana* glutamate-gated chloride channels, substantially purified forms of associated *S. americana* glutamate-gated chloride channels and recombinant membrane fractions comprising these proteins, associated mutant proteins, and methods associated with identifying compounds which modulate associated *Schistocerca americana* glutamate-gated chloride channels, which will be useful as insecticides.

BACKGROUND OF THE INVENTION

Dudel et al. (1989, *Brain Res.* 481: 215–220) demonstrated direct gating of an ion channel by glutamate in the arthropod, *Schistocerca gregaria* (locust) leg muscle.

Glutamate-gated chloride channels, or H-receptors, have been identified in arthropod nerve and muscle (Lingle et al, 1981, *Brain Res.* 212: 481–488; Horseman et al., 1988, *Neurosci. Lett.* 85: 65–70; Wafford and Sattelle, 1989, *J. Exp. Bio.* 144: 449–462; Lea and Usherwood, 1973, *Comp. Gen. Parmacol.* 4: 333–350; and Cull-Candy, 1976, *J. Physiol.* 255: 449–464).

Additionally, glutamate-gated chloride channels have been cloned from the soil nematode *Caenorhabditis elegans* (Cully et al., 1994, *Nature* 371: 707–711; see also U.S. Pat. No. 5,527,703 and Arena et al., 1992, *Molecular Brain Research.* 15: 339–348) and *Drosophila melanogaster* (Cully et al., 1996, *J. Biol. Chem.* 271: 20187–20191).

Raymond et al. (2000, *Neuroreport* 11: 2695–2701) disclose detection of GluCl channels in dorsal median neurons in *Periplanta americana* (cockroach).

Invertebrate glutamate-gated chloride channels are important targets for the widely used avermectin class of anthelmintic and insecticidal compounds. The avermectins are a family of macrocyclic lactones originally isolated from the actinomycete *Streptomyces avermitilis*. The semisynthetic avermectin derivative, ivermectin (22,23-dihydro-avermectin $B_{1a}$), is used throughout the world to treat parasitic helminths and insect pests of man and animals. The avermectins remain the most potent broad spectrum endectocides exhibiting low toxicity to the host. After many years of use in the field, there remains little resistance to avermectin in the insect population. The combination of good therapeutic index and low resistance strongly suggests that the glutamate-gated chloride (GluCl) channels remain good targets for insecticide development.

Despite the identification of the aforementioned cDNA clones encoding GluCl channels, it would be advantageous to identify additional invertebrate genes encoding GluCl channels in order to allow screening to identify novel GluCl channel modulators that may have insecticidal, mitacidal and/or nematocidal activity for animal health or crop protection. The present invention addresses and meets these needs by disclosing isolated nucleic acid molecules which express a *Schistocerca americana* GluGl channel wherein expression of grasshopper GluCl cRNA in *Xenopus* oocytes or other appropriate host cell results in an active GluCl channel. Heterologous expression of a *Schistocerca americana* (grasshopper) GluCl channels will allow the pharmacological analysis of compounds active against parasitic invertebrate species relevant to animal and human health. Such species include worms, fleas, tick, and lice. Heterologous cell lines expressing an active GluCl channel can be used to establish functional or binding assays to identify novel GluCl channel modulators that may be useful in control of the aforementioned species groups.

SUMMARY OF THE INVENTION

The present invention relates to an isolated or purified nucleic acid molecule (polynucleotide) which encodes a novel *Schistocerca americana* (grasshopper) invertebrate GluCl channel protein.

The present invention relates to an isolated of purified nucleic acid molecule (polynucleotide) which encodes mRNA which expresses a novel *Schistocerca americana* (grasshopper) invertebrate GluCl channel protein, this DNA molecule comprising the nucleotide sequence disclosed herein as SEQ ID NO:1, SEQ ID NO:3, SEQ ID NO:5, SEQ ID NO:7 and SEQ ID NO:9.

The present invention also relates to biologically active fragments or mutants of SEQ ID NOs:1, 3, 5, 7 and 9 which encodes mRNA expressing a novel *Schistocerca americana* (grasshopper) invertebrate GluCl channel protein. Any such biologically active fragment and/or mutant will encode either a protein or protein fragment which at least substantially mimics the pharmacological properties of a grasshopper GluCl channel protein, including but not limited to the grasshopper GluCl channel proteins as set forth in SEQ ID NO:2, SEQ ID NO:4, SEQ ID NO:6, SEQ ID NO:8 and SEQ ID NO:10. Any such polynucleotide includes but is not necessarily limited to nucleotide substitutions, deletions, additions, amino-terminal truncations and carboxy-terminal truncations such that these mutations encode mRNA which express a functional *S. americana* GluCl channel in a eukaryotic cell, such as *Xenopus* oocytes, so as to be useful for screening for agonists and/or antagonists of *S. americana* GluCl activity.

A preferred aspect of this portion of the present invention is disclosed in FIGS. 1A–F, cDNA molecule (SEQ ID NOs:1, 3, 5, 5 and 9) encoding a novel *Schistocerca americana* (grasshopper) GluCl protein.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

The present invention also relates to subcellular membrane fractions of the recombinant host cells (both prokaryotic and eukaryotic as well as both stably and transiently transformed cells) which contain the functional and processed proteins encoded by the nucleic acids of the present invention. The present invention relates to a substantially purified membrane preparation which comprises a *S. americana* GluCl channel and is essentially free from contaminating proteins, including but not limited to other *S. americana* source proteins or host proteins from a recombinant cell which expresses SaGluCl1 or SaGluCl2. Especially preferred is a membrane preparation which contains a *S. americana* GluCl channel comprising a GluCl protein comprising the functional form of the full length GluCl channel proteins as disclosed in FIGS. 2A–B and as set forth in SEQ ID NOs: 2, 4, 6, 8 and 10. To this end, the present invention also relates to a substantially purified membrane preparation which is purified from a recombinant host, whether a recombinant eukaryotic or recombinant prokaryotic host, wherein a recombinant vector expresses a functional and fully processed *S. americana* GluCl channel. Especially preferred is a membrane preparation which comprises a recombinant form of the *S. americana* GluCl channel, SaGluCl1, SaGluCl2 or any heteromultimer combination wherein a protein sequence comprises a functional portion of the full length SaGluCl proteins as disclosed in FIGS. 2A–B and as set forth in SEQ ID NOs: 2, 4, 6, 8 and 10. These subcellular membrane fractions will comprise either wild-type or mutant variations which are biologically functional forms of the *S. americana* GluCl channel, SaGluCl1, SaGluCl2 or any heteromultimer combination thereof at levels substantially above endogenous levels and hence will be useful in various assays described throughout this specification. A preferred eukaryotic host of choice to express the glutamate-gated channels of the present invention are *Xenopus* oocytes.

It is exemplified herein that expression of either DNA molecule encoding a short form of SaGluCl1 (i.e., SEQ ID NO:5 and/or 7) in *Xenopus* oocytes of chinese hamster ovary (CHO) cells results in a functional GluCl channel. In contrast, co-expression of SaGluCl2 (from, e.g., SEQ ID NO:9) with a short form of SaGluCl1 prevents the formation of a functional channel otherwise detectable when the short form of SaGluCl1 is expressed alone. Expression of either long form of SaGluCl1 is shown to be non-functional to date in *Xenopus* oocytes. The short form exemplified herein is expression of the "SC" form (SEQ ID NO:7, expression the precursor protein containing the amino acid sequence as set forth in SEQ ID NO:8, the expression in *Xenopus* oocytes or CHO cells resulting in formation of the functional GluCl channel).

The present invention also relates to a substantially purified form of an *S. americana* GluCl channel protein, which comprises the amino acid sequence disclosed in FIGS. 2A–B and set forth as SEQ ID NOs:2, 4, 6, 8 and 10.

A preferred aspect of this portion of the present invention is a an *S. americana* GluCl channel protein which consists of the amino acid sequence disclosed in FIGS. 2A–B and set forth as SEQ ID NOs:2, 4, 6, 8 and 10.

Another preferred aspect of the present invention relates to a substantially purified, fully processed GluCl channel protein obtained from a recombinant host cell containing a DNA expression vector comprises a nucleotide sequence as set forth in SEQ ID NOs: 1, 3, 5, 7, and/or 9 and expresses the respective SaGluCl precursor protein. It is especially preferred is that the recombinant host cell be a eukaryotic host cell, such as a mammalian cell line, or *Xenopus* oocytes, as noted above.

Another preferred aspect of the present invention relates to a substantially purified membrane preparation which has been obtained from a recombinant host cell transformed or transfected with a DNA expression vector which comprises and appropriately expresses a complete open reading frame as set forth in SEQ ID NOs: 1, 3, 5, 7, and/or 9, resulting in a functional, processed form of the respective SaGluCl channel. It is especially preferred is that the recombinant host cell be a eukaryotic host cell, such as a mammalian cell line, or *Xenopus* oocytes, as noted above.

The present invention also relates to biologically active fragments and/or mutants of an *S. americana* GluCl channel protein, comprising the amino acid sequence as set forth in SEQ ID NOs:2, 4, 6, 8 and/or 10, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/or antagonists for *S. americana* GluCl channel pharmacology.

A preferred aspect of the present invention is disclosed in FIGS. 2A–B and is set forth as SEQ ID NOs:2, 4, 6, 8 and 10, respective amino acid sequences which encode grasshopper GluCl proteins. Characterization of one or more of these channel proteins allows for screening methods to identify novel GluCl channel modulators that may have insecticidal, mitacidal and/or nematocidal activity for animal health or crop protection. As noted above, heterologous expression of a *Schistocerca americana* (grasshopper) GluCl channels will allow the pharmacological analysis of compounds active against parasitic invertebrate species relevant to animal and health. Such species include worms, fleas, tick, and lice. Heterologous cell lines expressing a functional SaGluCl channel (e.g., functional forms of SEQ ID NO:6 and 8, including but not limited to mature forms generated via heterologous expression of SEQ ID NO: 5 or 7) can be used to establish functional or binding assays to identify novel GluCl channel modulators that may be useful in control of the aforementioned species groups. Additionally, co-expression of a functional SaGluCl protein with SaGluCl2 results in SaGluCl2 imparting a dominant negative effect on channel activity, which is also useful in various assays utilized to identify modulators of an in vivo GluCl channel.

The present invention also relates to polyclonal and monoclonal antibodies raised in response to either the form of SaGluCl, or a biologically active fragment thereof.

The present invention also relates to SaGluCl1 and/or SaGlu2 fusion constructs, including but not limited to fusion constructs which express a portion of the SaGluCl1 and/or SaGlu2 linked to various markers, including but in no way limited to GFP (Green fluorescent protein), the MYC epitope, and GST. Any such fusion constructs may be expressed in the cell line of interest and used to screen for modulators of one or more of the SaGluCl proteins disclosed herein.

The present invention relates to methods of expressing grasshopper GluCl channel proteins biological equivalents disclosed herein, assays employing these gene products, recombinant host cells which comprise DNA constructs which express these proteins, and compounds identified through these assays which act as agonists or antagonists of GluCl channel activity.

It is an object of the present invention to provide an isolated nucleic acid molecule (e.g., SEQ ID NOs:1, 3, 5, 7, and 9) which encodes a novel form of grasshopper GluCl, or fragments, mutants or derivatives of SEQ ID NOs:2, 4, 6, 8 and 10. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for selective modulators for invertebrate GluCl pharmacology.

It is a further object of the present invention to provide the grasshopper GluCl proteins or protein fragments encoded by the nucleic acid molecules referred to in the preceding paragraph.

It is a further object of the present invention to provide recombinant vectors and recombinant host cells which comprise a nucleic acid sequence encoding grasshopper GluCl proteins or a biological equivalent thereof.

It is an object of the present invention to provide a substantially purified form of grasshopper GluCl proteins, as set forth in SEQ ID NOs:2, 4, 6, 8, and 10.

Is is another object of the present invention to provide a substantially purified recombinant form of a grasshopper GluCl protein which has been obtained from a recombinant host cell transformed or transfected with a DNA expression vector which comprises and appropriately expresses a complete open reading frame as set forth in SEQ ID NOs: 1, 3, 5, 7, and/or 9, resulting in a functional, processed form of the respective SaGluCl channel. It is especially preferred is that the recombinant host cell be a eukaryotic host cell, such as a mammalian cell line.

It is an object of the present invention to provide for biologically active fragments and/or mutants of grasshopper GluCl proteins, such as set forth in SEQ ID NOs:2, 4, 6, 8 and 10, including but not necessarily limited to amino acid substitutions, deletions, additions, amino terminal truncations and carboxy-terminal truncations such that these mutations provide for proteins or protein fragments of diagnostic, therapeutic and/or prophylactic use.

It is further an object of the present invention to provide for substantially purified subcellular membrane preparations which comprise pharmacologically active grasshopper GluCl channels, especially subcellular fractions obtained from a host cell transfected or transformed with a DNA vector comprising a nucleotide sequence which encodes a protein which comprises the amino acid as set forth in SEQ ID NO:2, 4, 6, 8 and 10 and FIGS. 2A–B.

Is is another object of the present invention to provide a substantially purified membrane preparations obtained from a recombinant host cell transformed or transfected with a DNA expression vector which comprises and appropriately expresses a complete open reading frame as set forth in SEQ ID NOs: 1, 3, 5, 7, and/or 9, resulting in a functional, processed form of the respective SaGluCl channel. It is especially preferred is that the recombinant host cell be a eukaryotic host cell, such as a mammalian cell line, or *Xenopus* oocytes.

It is also an object of the present invention to use grasshopper GluCl proteins or membrane preparations containing grasshopper GluCl proteins or a biological equivalent to screen for modulators, preferably selective modulators, of grasshopper GluCl channel activity. Any such compound may be useful in screening for and selecting compounds active against parasitic invertebrate species relevant to animal and health. Such species include worms, fleas, tick, and lice. These membrane preparations may be generated from heterologous cell lines expressing these GluCl and may constitute full length protein, biologically active fragments of the full length protein or may rely on fusion proteins expressed from various fusion constructs which may be constructed with materials available in the art.

As used herein, "substantially free from other nucleic acids" means at least 90%, preferably 95%, more preferably 99%, and even more preferably 99.9%, free of other nucleic acids. Thus, a grasshopper GluCl DNA preparation that is substantially free from other nucleic acids will contain, as a percent of its total nucleic acid, no more than 10%, preferably no more than 5%, more preferably no more than 1%, and even more preferably no more than 0.1%, of non-grasshopper GluCl nucleic acids. Whether a given grasshopper GluCl DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, an grasshopper GluCl protein preparation that is substantially free from other proteins will contain, as a percent of its total protein, no more than 10%, preferably no more than 5%, more preferably no more than 1%, and even more preferably no more than 0.1%, of non-grasshopper GluCl proteins. Whether a given grasshopper GluCl protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated grasshopper GluCl protein" or "purified grasshopper GluCl protein" also refer to grasshopper GluCl protein that has been isolated from a natural source. Use of the term "isolated" or "purified" indicates that grasshopper GluCl protein has been removed from its normal cellular environment. Thus, an isolated grasshopper GluCl protein may be in a cell-free solution or placed in a different cellular environment from that in which it occurs naturally. The term isolated does not imply that an isolated grasshopper GluCl protein is the only protein present, but instead means that an isolated grasshopper GluCl protein is substantially free of other proteins and non-amino acid material (e.g., nucleic acids, lipids, carbohydrates) naturally associated with the grasshopper GluCl protein in vivo. Thus, a grasshopper GluCl protein that is recombinantly expressed in a prokaryotic or eukaryotic cell and substantially purified from this host cell which does not naturally (i.e., without intervention) express this GluCl protein is of course "isolated grasshopper GluCl protein" under any circumstances referred to herein. As noted above, a grasshopper GluCl protein preparation that is an isolated or purified grasshopper GluCl protein will be substantially free from other proteins will contain, as a percent of its total protein, no more than 10%, preferably no more than 5%, more preferably no more than 1%, and even more preferably no more than 0.1%, of non-grasshopper GluCl proteins.

As used interchangeably herein, "functional equivalent" or "biologically active equivalent" means a protein which does not have exactly the same amino acid sequence as naturally occurring grasshopper GluCl, due to alternative splicing, deletions, mutations, substitutions, or additions, but retains substantially the same biological activity as grasshopper GluCl. Such functional equivalents will have significant amino acid sequence identity with naturally occurring grasshopper GluCl and genes and cDNA encoding such functional equivalents can be detected by reduced stringency hybridization with a DNA sequence encoding naturally occurring Grasshopper GluCl. For example, a naturally occurring grasshopper GluCl disclosed herein comprises the amino acid sequence shown as SEQ ID NO:2 and is encoded by SEQ ID NO:1. A nucleic acid encoding a functional equivalent has at least about 50% identity at the nucleotide level to SEQ ID NO:1.

As used herein, "a conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, "GluCl" refers to—L-glutamate-gated chloride channel—.

As used herein, the term "mammalian" will refer to any mammal, including a human being.

BRIEF DESCRIPTION OF THE DRAWINGS

FIGS. 1A–F compares the nucleotide sequence of the DNA molecules which encode respective grasshopper GluCl proteins, as set forth in SEQ ID NOs:1, 3, 5, 7, and 9.

FIGS. 2A–B show the amino acid sequence of the grasshopper GluCl proteins as set forth in SEQ ID NO:2, 4, 6, 8, and 10.

DETAILED DESCRIPTION OF THE INVENTION

The present invention relates to an isolated nucleic acid molecule (polynucleotide) which encodes a *Schistocerca americana* (grasshopper) invertebrate GluCl channel protein. The nucleic acid molecules of the present invention are substantially free from other nucleic acids. For most cloning purposes, DNA is a preferred nucleic acid.

The present invention relates to an isolated nucleic acid molecule (polynucleotide) which encodes mRNA which expresses a novel *Schistocerca americana* (grasshopper) invertebrate GluCl channel protein, this DNA molecule comprising the nucleotide sequence disclosed herein as SEQ ID NO:1, SEQ ID NO:3, SEQ ID NO:5, SEQ ID NO:7 and SEQ ID NO:9.

Figure 3:
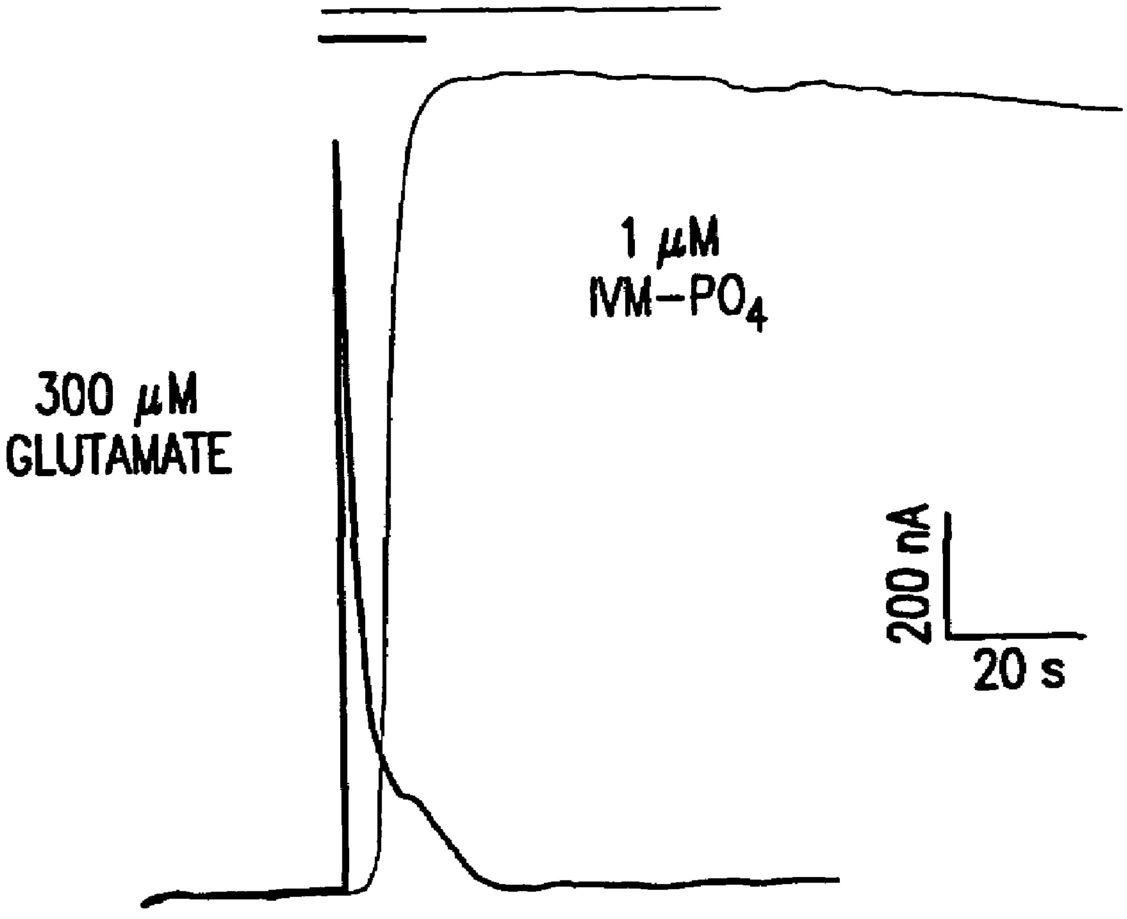
FIG. 3 shows the results of an experiment in which the clone SaGluCl1 (short form "SC") was expressed in a *Xenopus* oocyte. The measurement is made with the two microelectrode voltage clamp technique and the membrane potential was held at 0 mV. Two current recordings are superimposed. The bars at top show the duration of application of glutamate and ivermectin phosphate.

The isolation and characterization of the SaGluCl nucleic acid molecules of the present invention were identified through degenerate PCR as described in detail in Example Section 1. PCR products of the appropriate size were cloned into the PCR2.1 plasmid vector using a "TA" cloning kit (Invitrogen, Inc.). Following sequence analysis (ABI Prism, PE Applied Biosystems), selected PCR clone inserts were radiolabelled and used as probes to screen a cDNA library generated into the Uni-ZAP vector (Stratagene, Inc.) from using and a poly (A) enriched fraction from the RNA mentioned above. Sequences from full-length cDNA clones were analyzed using the GCG Inc. package. Subcloning of SaGluCl1 clones and of SaGluCl2 into a mammalian expression vector was done by excision of whole inserts (EcoRI+XhoI excision) from the UniZap pBS plasmid, followed by ligation into the TetSplice (Life Technologies Inc.). Invertebrate glutamate-gated chloride channels (GluCls) are related to the glycine- and GABA-gated chloride channels and are distinct from the excitatory glutamate receptors (e.g. NMDA or AMPA receptors). The first two members of the GluCl family were identified in the nematode *C. elegans*, following a functional screen for the receptor of the anthelmintic drug ivermectin. Several additional GluCls have now been cloned in other invertebrate species. However, there is no evidence yet for GluCl counterparts in vertebrates; because of this, GluCls are excellent targets for anthelmintics, insecticides, acaricides, etc. Specific GluCl modulators, such as nodulasporic acid and its derivatives, indeed have an ideal safety profile because they lack mechanism-based toxicity in vertebrates. The present invention relates in part to two novel GluCl clones, SaGluCl1 and GluCl2, from the ventral ganglia of the grasshopper *Schistocerca americana* by reverse-transcriptase polymerase chain reaction (RT-PCR) using degenerate oligonucleotides as reaction primers. Sequence data of full-length SaGluCl1 cDNA clones (SEQ ID NOs: 1, 3, 5, and 7) shows homology to *D. melanogaster* DrosGluClα and to *C. felis* CfGluCl DNA. Heterologous expression of the short form of SaGluCl1 into *Xenopus laevis* oocytes results in a robust L-glutamate-gated chloride current. This channel is also activated by nodulasporic acid and ivermectin. Sequence of full-length SaGluCl2 cDNA clone (SEQ ID NO;9) shows a moderate homology with various GluCls. Co-expression of SaGluCl2 with SaGluCl1 strongly reduces the response to the compounds mentioned above, suggesting a modulator role for SaGluCl2. From previous work on other four-transmembrane ligand-gated channels receptors (Acetylcholine, GABA receptors, etc.) it emerges that most, if not all, native channels are heteromultimers, i.e. pentamers that include at least two different subunits. In an attempt to demonstrate that SaGluCl1 and SaGluCl2 can co-assemble into a functional channel, both clones were co-expressed in *Xenopus* oocytes and CHO cells. No current was observed in either case when both clones were co-expressed. It therefore appears that, under these heterologous expression conditions, SaGluCl2 has a dominant negative effect on SaGluCl1. Since data nevertheless indicate that both subunits are highly expressed in the same neurons, a third component of the native GluCl possibly remains to be identified. Alternatively, the possibility remains that SaGluCl1 and SaGluCl2 are not expressed within common (neuronal) cells within the ganglia and may not co-assemble into a common, functional channel. Regardless, as shown in FIG. 3 (*Xenopus* oocytes) and FIGS. 4A and 4B (CHO cells), expression of the short form of SaGluCl1 results in formation of a functional homomultimer channel, responsive to glutamate, ivermectin and nodulasporic acid.

Therefore, SaGluCl2, when co-expressed with the short form of SaGluCl1, prevents the formation of a functional channel otherwise detectable with SaGluCl1 alone. The SaGluCl2 protein is therefore expressed, acting as a modulator of SaGluCl1. Both SaGluCl1 and SaGluCl2 are expressed in the same tissue and this tissue shows GluCl activity as recorded electrophysiologically. Therefore, either 1) SaGluCl1 and SaGluCl2 are not expressed in the exact same cells and/or 2) there is an additional, yet to be identified factor which is either be another SaGluCl form, or an unrelated type of protein such as that seen with the TipE protein from *Drosophila*, which enhances in vitro expression of the para sodium channel (see Feng et al., 1995, *Cell* 82:1001–1011). It has also been shown that SaGluCl2 can negatively affect non-SaGluCl four-transmembrane ligand-gated ion channels (4TMLGIC), but does not likely exert any effect on other type of ion channels. Therefore, the SaGluCl protein may be classified as a potential broad spectrum inhibitory subunit as it relates specifically to four-transmembrane ligand-gated ion channels, lending this isolated cDNA clones, associated vectors, hosts, recombinant subcellular fractions and membranes, and the expressed and mature forms of SaGluCl2 as important tools for drug discovery.

To this end, the present invention relates in part to transgenic animals, either an invertebrate (e.g., *C. elegans*) or vertebrate (e.g., mouse), for which the gene encoding SaGluCl2 has been introduced into the germline of the animal. The purpose of this would be to inactivate, in the host, one or several endogenous 4TMLGIC and observe the biological effects. One such effect may well be an acquired resistance to drugs that are agonists (activators) of 4TMLGIC. In the case of drugs with suspected—but unproven—method of action (MOA) via 4TMLGIC, such SaGluCl2-harboring transgenic animals may be used to confirm such an effect. Expression of the newly introduced gene encoding SaGluCl2 into the host can be constitutive or inducible, depending on the type of promoter used to drive its expression. Also depending on the type of promoter used, expression of SaGluCl2 can be targeted to a given tissue(s) or it can be generalized. The same logic can be applied to in vitro expression in e.g. *Xenopus* oocytes. Co-expression of SaGluCl2 with any other 4TMLGIC (including functional SaGluCl1 forms as well as non-locust forms) should prevent any 4TMLGIC-mediated current. *Xenopus* oocytes may be injected with mixed populations of RNA or mRNA from e.g. mammalian brain or from whole animals (e.g. *C. elegans*). These oocytes are then subjected to drugs of sometimes unknown MOA. The use of SaGluCl2 may lead to inhibition of the drug response, hence narrowing down the investigative process to 4TMLGICs and in turn helping to identify preferred modulators of various 4TLMGICs.

Therefore, the heterologous expression of grasshopper GluCl channels, especially SaGluCl1 alone or the co-expression of SaGluCl2 as described above, will allow the pharmacological analysis of compounds active against parasitic invertebrates species relevant to animal and human health. Such species include worms, fleas, tick, and lice. Heterologous cell lines expressing these GluCl channels can be used to establish functional or binding assays to identify novel GluCl channel modulators that may be useful in control of the aforementioned species groups.

The DNA molecule described in FIGS. 1A–F as SAGluCl1LA (Sa1LA) and set forth as SEQ ID NO:1, which encodes the grasshopper GluCl protein described in FIGS. 2A–B as 1LA and set forth as SEQ ID NO:2, the nucleotide sequence as follows:

GCCGCACGTG CCGCACGCCT CGCCACGCCG CAC-CGCAGGT CTCTTCGCCC ATGGAGGAGC TCGTGC-GACT GGAGTGAGCT TGTGGCTTAC GGCTCTATCC GAGGAACCAT AAGCAAGTCA CCGGCAGTTG AGGGTTAACT GGTAATGCGG GCGCGGGTCG AGGCCAGCAG AGACCGCCGC GTGCCGCCCG CGGACTCGCA CTGCCCCCCG GACGCGCCGC CCCGGCCGCC AGCCGCGCGC TCGCCCTGCT CCCACCGCCT CTGAAGTTCG AGGGACAGCT CAGCCTCAGC ATCCCTACAG GAACCATGAT GAGC-GACCTC TGCAAGACGC CGTGGTGGCT TTGT-GCGCTG CTGTTGCTGG CCGCCAACGT GCCAGAT-GCC TGGTGCACGC AGCAGAAGAT GAACTTCCGC GAGAAGGAGA AACAGGTGCT GGACCAGATC CTGGGGCCAG GTCGCTACGA CGCGCGCATC CGGCCGTCGG GGATCAACGG CACAGCGGAC AAC-CCCACCA TAGTGAAAGT GAACATCTTC CTTCGCTCTA TCAGCAAAAT AGACGATTAT AAAAT-GATGT TCCGCTGCGC TGCCCCGCTT GCATGCCGCC CGGACCCCGC ACGCCGCCCT CGGCCCAGCG TCAT-GTGTTT TGTTACACGT GTTCTCAACA GGAGC-CAGGC TCACCGACCC GGCCGCCAAT CAGGCGC-CGC GTGTGCGACT CCGAACAAGG AATACAGCGT CCAGCTGACA TTCAGAGAGC AGTGGATGGA TGAGCGGCTC AAGTTCAATG ACTTCAAAGG AAAAATAAAG TACCTGACAC TGACAGACGC CAA-CAGAGTA TGGATGCCAG ATTTATTTTT CTCTAAC-GAA AAGGAAGGAC ATTTTCATAA CATTATCATG CCCAACGTTT ATATACGTAT TTTTCCTTAT GGATCG-GTGC TCTACAGTAT CAGAATCTCT CTGACSCTCT CCTGCCCGAT GAACCTGAAG CTGTACCCGC TCGA-CAGGCA GGTCTGCTCG CTGAGGATGG CCAGC-TATGG TTGGACGACT GATGACCTGG TGTTCCTGTG GAAAGACGGC GACCCGGTGC AGGTGGTCAA GAACCTGCAC CTGCCGCGCT TCACGCTAGA GAAGTTCCTT ACCGACTACT GCAACAGCAA AAC-TAACACA GGAGAGTACA GCTGCTTGAA GGTG-GACCTG CTGTTCAACC GCGAGTTCAG CTACTAC-CTG ATCCAGATCT ACATCCCGTG CTGCATGCTG GTGATAGTGT CGTGGGTGTC CTTCTGGCTC GAT-CAGAGCG CCATCCCGGC ACGGGTGTCC CTAG-GCGTGA CCACGCTGCT CACCATGGCC ACCCA-GACGT CGGGCATCAA CGCCTCCCTG CCCCCCGTGT CCTATACCAA AGCCATCGAC GTGTGGACTG GCGTGTGCCT CACTTTCGTG TTCG-GCGCGT TGCTCGAGTT CGCGCTCGTC AAC-TACGCGA GCCGCTCGGA CATGCACCGC GAGAA-CATGA AGAAGCAGCG CCGCCAGGTA GAGCTGGAGC ACGCCGCGCA GCTCGAGGCG GCCGCTGACC TGCTCGTGGA GGACGGCAGC ACCACCTTTG CCATGAAGCC GTTGGTGGGA CAC-CCGGGCG GTCCGGCGGC CGCAGCGCCC GGC-CTCGCAG GCCTGGACAA GGTGCGCCAG TGC-GAGATCC ACATGCAGCC CAAGCGCGAA AACTGCTGCC GCACCTGGCT CTCCAAGTTC CCCACGCGCT CCAAGCGCAT CGACGTCATC TCGCGCATCA CCTTCCCGCT CGTCTTCGCG CTCT-TCAACC TCGTCTACTG GTCCACCTAC CTGTTC-CGCG AGGACGAACG CGAGTGAGCC GCCAGC-CGCC ATCGCAGCAG CAGCCAGCT (SEQ ID NO:1).

The DNA molecule described in FIGS. 1A–F as SAGluCl1LC (Sa1LC) and set forth as SEQ ID NO:3, which encodes the grasshopper GluCl protein described in FIGS. 2A–B as 1LC and set forth as SEQ ID NO:4, the nucleotide sequence as follows:

GCCGCACGTG CCGCACGCCT CGCCACGCCG CACCGCAGGT CTCTTCGCCC ATGGAGGAGC TCGTGCGACT GGAGTGAGCT TGTGGCTTAC GGCTCTATCC GAGGAACCAT AAGCAAGTCA CCGGCAGTTG AGGGTTAACT GGTAATGCGG GCGCGGGTCG AGGCCAGCAG AGACCGCCGC GTGCCGCCCG CGGACTCGCA CTGCCCCCCG GACGCGCCGC CCCGGCCGCC AGCCGCGCGC TCGCCCTGCT CCCACCGCCT CTGAAGTTCG AGGGACAGCT CAGCCTCAGC ATCCCTACAG GAACCATGAT GAGCGACCTC TGCAAGACGC CGTGGTGGCT TTGTGCGCTG CTGTTGCTGG CCGCCAACGT GCCAGATGCC TGGTGCACGC AGCAGAAGAT GAACTTCCGC GAGAAGGAGA AACAGGTGCT GGACCAGATC CTGGGGCCAG GTCGCTACGA CGCGCGCATC CGGCCGTCGG GGATCAACGG CACAGCGGAC AACCCCACCA TAGTGAAAGT GAACATCTTC CTTCGCTCTA TCAGCAAAAT AGACGATTAT AAAATGATGT TCCGCTGCGC TGCCCCGCTT GCATGCCGCC CGGACCCCGC ACGCCGCCCT CGGCCCAGCG TCATGTGTTT TGTTACACGT GTTCTCAACA GGAGCCAGGC TCACCGACCC GGCCGCCAAT CAGGCGCCGC GTGTGCGACT CCGAACAAGG AATACAGCGT CCAGCTGACA TTCAGAGAGC AGTGGATGGA TGAGCGGCTC AAGTTCAATG ACTTCAAAGG AAAAATAAAG TACCTGACAC TGACAGACGC CAACAGAGTA TGGATGCCAG ATTTATTTTT CTCTAACGAA AAGGAAGGAC ATTTTCATAA CATTATCATG CCCAACGTTT ATATACGTAT TTTTCCTTAT GGATCGGTGC TCTACAGTAT CAGAATCTCT CTGACSCTCT CCTGCCCGAT GAACCTGAAG CTGTACCCGC TCGACAGGCA GGTCTGCTCG CTGAGGATGG CCAGCTATGG TTGGACGACT GATGACCTGG TGTTCCTGTG GAAAGACGGC GACCCGGTGC AGGTGGTCAA GAACCTGCAC CTGCCGCGCT TCACGCTAGA GAAGTTCCTT ACCGACTACT GCAACAGCAA AACTAACACA GGAGAGTACA GCTGCTTGAA GGTGGACCTG CTGTTCAAGC GCGAGTTCAG CTACTACCTG ATCCAGATCT ACATCCCGTG CTGCATGCTG GTGATAGTGT CGTGGGTGTC CTTCTGGCTC GATCAGAGCG CCATCCCGGC ACGGGTGTCC CTAGGCGTGA CCACGCTGCT CACCATGGCC ACCCAGACGT CGGGCATCAA CGCCTCCCTG CCCCCCGTGT CCTATACCAA AGCCATCGAC GTGTGGACTG GCGTGTGCCT CACTTTCGTG TTCGGCGCGT TGCTCGAGTT CGCGCTCGTC AACTACGCGA GCCGCTCGGA CATGCACCGC GAGAACATGA AGAAGCAGCG CCGCCAGGTA GAGCTGGAGC ACGCCGCGCA GCTCGAGGCG GCCGCTGACC TGCTCGTGGA GGACGGCAGC ACCACCTTTG CCATGAAGCC GTTGGTGGGA CACCCGGGCG GTCCGGCGGC CGCAGCGCCC GGCCTCGCAG GCCTGGACAA GGTGCGCCAG TGCGAGATCC ACATGCAGCC CAAGCGCGAA AACTGCTGCC GCACCTGGCT CTCCAAGTTC CCCACGCGCT CCAAGCGCAT CGACGTCATC TCGCGCATCA CCTTCCCGCT CGTCTTCGCG CTCTTCAACC TCGTCTACTG GTCCACCTAC CTGTTCCGCG AGGACGACCG CGAGTGAGCC GCCAGCCGCC ATCGCAGCAG CAGCCAGCT (SEQ ID NO:3).

The DNA molecule described in FIG. 1A–F as SAGluCl1SA (Sa1SA) and set forth as SEQ ID NO:5, which encodes the grasshopper GluCl protein described in FIGS. 2A–B as 1SA and set forth as SEQ ID NO:6, the nucleotide sequence as follows:

AGCAGTGGCG CGACTACCGC CGCACGTGCC GCACCCCTCG CCACGCCGCA CCGCAGGTCT CTTCGCTCAT GGAGGAGCTC GTGCGACTGG AGTGAGCGTG TGGCTTACGG CTCTATCCGA GGAACCATAA GCAACAGTCA CCGGCAGTTG AGGGTTAACT GGTAATGCGG GCGCGGGTCG AGGCCAGCAG AGACCGCCGC GTGCCGCCCG CGGACTCGCA CTGCCCCCCG GACGCGCCGC CCCGGCCGCC AGCCGCGCGC TCGCCCTGCT CCCGCCGCCT CTGAAGTCCA AGGGTTAGCT CAGCCTCAGC ATCCCTGCAG GAACCATGAT GAGCGACCTC TGCAAGACGC CGTGGTGGCT TTGTGCGCTG CTGTTGCTGG CCGCCAACGT GCCAGATGCC TGGTGCACGC AGCAGAAGAT GAACTTCCGC GAGAAGGAGA AACAGGTGCT GGACCAGATC CTGGGGCCAG GTCGCTACGA CGCTCGCATC CGGCCGTCGG GGATCAACGG CACAGCGGAC AACCCCACCA TAGTGAAAGT GAACATCTTC CTTCGCTCTA TCAGCAAAAT AGACGATTAT AAAATGGAAT ACAGCGTCCA GCTGACATTC AGAGAGCAGT GGATGGATGA GCGGCTCAAG TTCAATGACT TCAAAGGAAA AATAAAGTAC CTGACACTGA CAGACGCCAA CAGAGTATGG ATGCCAGATT TATTTTTCTC TAACGAAAAG GAAGGACATT TTCATAACAT TATCATGCCC AACGTTTATA TACGTATTTT TCCTTATGGA TCGGTGCTCT ACAGTATCAG AATCTCTCTG ACGCTCTCCT GCCCGATGAA CCTGAAGCTG TACCCGCTCG ACAGGCAGGT CTGCTCGCTG AGGATGGCCA GCTATGGTTG GACGACTGAT GACCTGGTGT TCCTGTGGAA AGACGGCGAC CCGGTGCAGG TGGTCAAGAA CCTGCACCTG CCGCGCTTCA CGCTAGAGAA GTTCCTTACC GACTACTGCA ACAGCAAAAC CAACACAGGA GAGTACAGCT GCTTGAAGGT GGACCTGCTG TTCAAGCGCG AGTTCAGCTA CTACCTGATC CAGATCTACA TCCCGTGCTG CATGCTGGTG ATAGTGTCGT GGGTGTCCTT CTGGCTCGAT CAGAGCGCCA TCCCGGCACG GGTGTCCCTA GGCGTGACCA CGCTGCTCAC CATGGCCACC CAGACGTCGG GCATCAACGC CTCCCTGCCC CCCGTGTCCT ATACCAAAGC CATCGACGTG TGGACTGGCG TGTGCCTCAC TTTCGTGTTC GGCGCGTTGC TCGAGTTCGC GCTCGTCAAC TACGCGAGCC GCTCGGACAT GCACCGCGAG AACATGAAGA AGCAGCGCCG CCAGGTAGAG CTGGAGCACG CCGCGCAGCT CGAGGCGGCC GCTGACCTGC TCGTGGAGGA CGGCAGCACC ACCTTTGCCA TGAAGCCGTT GGTGGGACAC CCGGGCGGTC CGGCGGCCGC AGCGCCCGGC CTCGCAGGCC TGGACAAGGT GCGCCAGTGC GAGATCCACA TGCAGCCCAA GCGCGAAAAC TGCTGCCGCA CCTGGCTCTC CAAGTTCCCC ACGCGCTCCA AGCGCATCGA CGTCATCTCG CGCATCACCT TCCCGCTCGT CTTCGCGCTC TTCAACCTCG TCTACTGGTC CACCTACCTG TTCCGCGAGG ACGAACGCGA GTGAGCCGCC AGCCGCCATC GCAGCAGCAG CCAAGCTACG TGGGGACGTC ATCGCC (SEQ ID NO:5).

The DNA molecule described in FIG. 1A–F as SAGluCl1SC (Sa1SC) and set forth as SEQ ID NO:7, which encodes the grasshopper GluCl protein described in FIGS. 2A–B as 1SC and set forth as SEQ ID NO:8, the nucleotide sequence as follows:

AGCAGTGGCG CGACTACCGC CGCACGTGCC GCACGCCTCG CCACGCCGCA CCGCAGGTCT CTTCGCTCAT GGAGGAGCTC GTGCGACTGG AGTGAGCGTG TGGCTTACGG CTCTATCCGA GGAACCATAA GCAACAGTCA CCGGCAGTTG AGGGTTAACT GGTAATGCGG GCGCGGGTCG AGGCCAGCAG AGACCGCCGC GTGCCGCCCG CGGACTCGCA CTGCCCCCCG GACGCGCCGC CCCGGCCGCC AGCCGCGCGC TCGCCCTGCT CCCGCCGCCT CTGAAGTCCA AGGGTTAGCT CAGCCTCAGC ATCCCTGCAG GAACCATGAT GAGCGACCTC TGCAAGACGC CGTGGTGGCT TTGTGCGCTG CTGTTGCTGG CCGCCAACGT GCCAGATGCC TGGTGCACGC AGCAGAAGAT GAACTTCCGC GAGAAGGAGA AACAGGTGCT GGACCAGATC CTGGGGCCAG GTCGCTACGA CGCTCGCATC CGGCCGTCGG GGATCAACGG CACAGCGGAC AACCCCACCA TAGTGAAAGT GAACATCTTC CTTCGCTCTA TCAGCAAAAT AGACGATTAT AAAATGGAAT ACAGCGTCCA GCTGACATTC AGAGAGCAGT GGATGGATGA GCGGCTCAAG TTCAATGACT TCAAAGGAAA AATAAAGTAC CTGACACTGA CAGACGCCAA CAGAGTATGG ATGCCAGATT TATTTTTCTC TAACGAAAAG GAAGGACATT TTCATAACAT TATCATGCCC AACGTTTATA TACGTATTTT TCCTTATGGA TCGGTGCTCT ACAGTATCAG AATCTCTCTG ACGCTCTCCT GCCCGATGAA CCTGAAGCTG TACCCGCTCG ACAGGCAGGT CTGCTCGCTG AGGATGGCCA GCTATGGTTG GACGACTGAT GACCTGGTGT TCCTGTGGAA AGACGGCGAC CCGGTGCAGG TGGTCAAGAA CCTGCACCTG CCGCGCTTCA CGCTAGAGAA GTTCCTTACC GACTACTGCA ACAGCAAAAC CAACACAGGA GAGTACAGCT GCTTGAAGGT GGACCTGCTG TTCAAGCGCG AGTTCAGCTA CTACCTGATC CAGATCTACA TCCCGTGCTG CATGCTGGTG ATAGTGTCGT GGGTGTCCTT CTGGCTCGAT CAGAGCGCCA TCCCGGCACG GGTGTCCCTA GGCGTGACCA CGCTGCTCAC CATGGCCACC CAGACGTCGG GCATCAACGC CTCCCTGCCC CCCGTGTCCT ATACCAAAGC CATCGACGTG TGGACTGGCG TGTGCCTCAC TTTCGTGTTC GGCGCGTTGC TCGAGTTCGC GCTCGTCAAC TACGCGAGCC GCTCGGACAT GCACCGCGAG AACATGAAGA AGCAGCGCCG CCAGGTAGAG CTGGAGCACG CCGCGCAGCT CGAGGCGGCC GCTGACCTGC TCGTGGAGGA CGGCAGCACC ACCTTTGCCA TGAAGCCGTT GGTGGGACAC CCGGGCGGTC CGGCGGCCGC AGCGCCCGGC CTCGCAGGCC TGGACAAGGT GCGCCAGTGC GAGATCCACA TGCAGCCCAA GCGCGAAAAC TGCTGCCGCA CCTGGCTCTC CAAGTTCCCC ACGCGCTCCA AGCGCATCGA CGTCATCTCG CGCATCACCT TCCCGCTCGT CTTCGCGCTC TTCAACCTCG TCTACTGGTC CACCTACCTG TTCCGCGAGG ACGACCGCGA GTGAGCCGCC AGCCGCCATC GCAGCAGCAG CCAAGCTACG TGGGGACGTC ATCGCC (SEQ ID NO:7).

The DNA molecule described in FIG. 1A–F as SaGluCl2 and set forth as SEQ ID NO:9, which encodes the grasshopper GluCl protein described in FIG. 2A–B as “2” and set forth as SEQ ID NO:10, the nucleotide sequence as follows:

GGCACGAGGG CGTCTCGGCT GTCCACACAC AGCAGGAATC ATGCTGAGCG CAACACCCAG CAAGCTGCGG CGATTTTGTG CTTTGGTGCT GTTGGTTGTG AATCTGTCAA AAGTCACATG CTCGGATCAG AAGACTAACA TCCGGGAGGC GGAGAGGCAG GTGATGGAGC ACGTCCTGAG CCCGAGCCCGC TACGACGCGC GGCTGCGGCC CCCGGGATAC AACGGCACAG AGAGTCCCAC TGTGGTAAAA GTTAACATCT TTGTACGCTC CATCAGCAGA GTAGATGATC AGCATATGGA ATATGACGCG CAGTTGACGT TCAGAGAGCA GTGGTTTGAC GACAGGCTCA AGTTTGACGA TTTTGGAGGT AAAATCAAAT ATCTAACACT GACAGATCCC AGCAGAATAT GGATGCCAGA TTTATTTTTT AGCAACGAGA AGAAAGCACA CTTTCACGAT GTAGTAATGC CTAATGTCTA TGTACGAATA TTTCCTCTTG GGTCGGTTCT CTACAGTACC AGAATCTCAA TGACACTCTC GTGTCCCATG GACCTGAGGC TGTACCCACA CGATCGACAG GTGTGCTCCA TCAGGATGGC CAGCTATGGT TGGACGACTG AAGACCTGGT GTTCATGTGG AAAGACGGCG ACCCGGTGCA GGTGGTCAAG AACCTGCGCC TTCCACGCTT CACGCTAGAG AAGTTCGTTA CTGATTACTG CCACGCCAGG ACAAACACAG GCGAGTACAG CTGCCTTAAA GTGGAACTGG TGTTTAAACG CGAGTTCCGC TACTACATGG TGCACATCTA CATTCCGACT TTCATGCTGG TGATAGTGTC GTGGCTATCG TTCTGGCTGG ATCAGAGAGC CATCACGGCA CGGACGTGCC TGGTGGTCAC GACGGTGCTC ACCATCACCA TCCAGACCTC GGGCGTCAGA AAGTCGCTGC CCGTCGTCAA CTACGTCATG GCCGTCGAGG TGTGGCTCGG GATGTGCGTC TCGTTCGTGT TCGGCGCACT GCTGCAGCTG GCGCTGGTCA ACTACCTGGC CCGCAAAGAG GCGTGCCGAG GCGCCGCCAA GCGGCACAAC CGCCTCGTCG GCCCGGAGCA CTCTGCACAG CTGGAGGAGA TCAGCGAGGC TCTCGTCGAG GACGGCAGCG CGGCATTCGC TATGAAGCTG CTGGAGGAGC AGTCAAACAG CCCCACGGCT GACAAGGAGG CGGCGGCCCA GGGCGGAAGG TGCTCGCCGC GGCAGTGGTG GCGCTCCTGG ATGGCCAGCT TCCCCACGGG CTCGCAGCGC GCCGATGCCG CATCGCGCGT CCTCTTCCCT CTCGCCTTCT CCCTCTTCTG CCTCGCCTAC TGGTGTGTCA ACGCCTCCGG ATAACAGCAA CACCAGTTGC TCGGCAGTGT CCTACGATGG TGGTGGAAGT AACCCTCCAC ACATATTTGC AGATGCACAA GCATTTATAC CTATTATAGA ATGAAAAATA AGTATTAAAG TACTGTATAA TTCTCTATTC ATCATTACTC TTACTGTATC GACATTACTG TTTGACGGCA ATTTCGTTAT ACGAGATTTG TCCGGAAAAT ACGCATAAAA GTTGAATTAT AACTTTATTT TACAATTATT CAGGTATTAC AATATGGTCT CCTTCAAAGT ACTCGCCCTG AGATGCGATA CACTGCTGTC AACGCCGTTT ACACTGTTGA TAATATTGCT GAAAGTCTTC AGTTGTGATG TTGTTCAGTT GCCGTGTCGT TTCCGCCTTG TGGCTTCCAC ATCTCCCAAG TGCCGCCCTC GAAGCACGAT TTTGCATTTC TGGAACATGA AGAAGTCACA TGGGGCTAAA GCGGGTGAAT AAGGCGGGTG GTCTGTCACG GTGATTGAGC TTCAGGCCAA AAACTCGCGC ACAACGAGCG ACGTGTGAGC GGGCGCTTTG TCGTGCTGAA GGATCCACCT GCCCCCTTTT GCCAACTCCG GTCGAACTCG GGCCACACGA GCTCTGAGAC GTGTCAGAAC TTCAACGTAA

AAATTTCCGT TCACTCTCTG GCCGGGAAGG ACAAATTCCT TGTG (SEQ ID NO:9).

The above-exemplified isolated DNA molecules, shown in FIG. 1A–F comprise the following characteristics:

SAGluCl1L (Sa1LA; SEQ ID NO:1):

1879 nuc.: initiating Met (nuc. 306–308) and "TGA" term. codon (nuc. 1845–1847);

SAGluCl1L (Sa1LC; SEQ ID NO:3):

1879 nuc.: initiating Met (nuc. 306–308) and "TGA" term. codon (nuc. 1845–1847);

SAGluCl1S (Sa1SA; SEQ ID NO:5):

1776 nuc.: initiating Met (nuc. 326–328) and "TGA" term. codon (nuc. 1712–1713);

SAGluCl1S (Sa1SC; SEQ ID NO:7):

1776 nuc.: initiating Met (nuc. 326–328) and "TGA" term. codon (nuc. 1712–1713);

SAGluCl2 (Sa2; SEQ ID NO:9):

2074 nuc.: initiating Met (nuc. 41–43) and "TGA" term. codon (nuc. 1382–1384).

In regard to the "long" form of SaGluCl1, the "LA"cDNA (SEQ ID NO:1) encodes a protein with a Glu residue at amino acid number 511, whereas the "LC cDNA (SEQ ID NO:3) encodes a protein with a Asp residue at amino acid number 511.

In regard to the "short" form of SaGluCl1, the "SA"cDNA (SEQ ID NO:5) encodes a protein with a Glu residue at amino acid number 460, whereas the "SC cDNA (SEQ ID NO:7) encodes a protein with a Asp residue at amino acid number 460.

The present invention also relates to biologically active fragments or mutants of SEQ ID NOs:1, 3, 5, 7 and 9 which encode mRNA expressing SaGluCl1 or SaGluCl2, respectively. Any such biologically active fragment and/or mutant will encode either a protein or protein fragment which at least substantially mimics the wild type protein, including but not limited to the wild type forms as set forth in SEQ ID NOs:2, 4, 6, 8 and/or 10. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for SaGluCl function.

A preferred aspect of this portion of the present invention is disclosed in FIGS. 1A–F, which describes the cDNA molecule encoding various forms of SaGluCl channel proteins.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The degeneracy of the genetic code is such that, for all but two amino acids, more than a single codon encodes a particular amino acid. This allows for the construction of synthetic DNA that encodes the SaGluCl protein where the nucleotide sequence of the synthetic DNA differs significantly from the nucleotide sequence of SEQ ID NOs:1, 3, 5, 7 and 9 but still encodes the same SaGluCl protein as SEQ ID NO:1, 3, 5, 7, and 9. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the SaGluCl channel protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (Computational Molecular Biology, Lesk, A. M., ed. Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptide sequences, the term "identity" is well known to skilled artisans (Carillo and Lipton, 1988, *SIAM J Applied Math* 48:1073). Methods commonly employed to determine identity or similarity between two sequences include, but are not limited to, those disclosed in Guide to Huge Computers, Martin J. Bishop, ed., Academic Press, San Diego, 1994, and Carillo and Lipton, 1988, *SIAM J Applied Math* 48:1073. Methods to determine identity and similarity are codified in computer programs. Preferred computer program methods to determine identity and similarity between two sequences include, but are not limited to, GCG program package (Devereux, et al, 1984, *Nucleic Acids Research* 12(1):387), BLASTN, and FASTA (Altschul, et al., 1990, *J. Mol. Biol.* 215:403). As an illustration, by a polynucleotide having a nucleotide sequence having at least, for example, 95% "identity" to a reference nucleotide sequence of SEQ ID NO:1, 3, 5, 7 and/or 9 is intended that the nucleotide sequence of the polynucleotide is identical to the reference sequence except that the polynucleotide sequence may include up to five point mutations or alternative nucleotides per each 100 nucleotides of the reference nucleotide sequence of SEQ ID NO:1, 3, 5, 7 and/or 9. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations or alternative nucleotide substitutions of the reference sequence may occur at the 5' or 3' terminal positions of the reference nucleotide sequence or anywhere between those terminal positions, interspersed either individually among nucleotides in the reference sequence or in one or more contiguous groups within the reference sequence. One source of such a "mutation" or change which results in a less than 100% identity may occur through RNA editing. The process of RNA editing results in modification of an mRNA molecule such that use of that modified mRNA as a template to generate a cloned cDNA may result in one or more nucleotide changes, which may or may not result in a codon change. This RNA editing is known to be catalyzed by an RNA editase. Such an RNA editase is RNA adenosine deaminase, which converts an adenosine residue to an inosine residue, which tends to mimic a cytosine residue. To this end, conversion of an mRNA residue from A to I will result in A to G transitions in the coding and noncoding regions of a cloned cDNA (e.g., see Hanrahan et al, 1999, *Annals New York Acad. Sci.* 868:51–66; for a review see Bass, 1997, *TIBS* 22: 157–162). Similarly, by a polypeptide having an amino acid sequence having at least, for example, 95% identity to a reference amino acid sequence of SEQ ID NO:2, 4, 6, 8 and/or 10 is intended that the amino acid sequence of the polypeptide is identical to the reference sequence except that the polypeptide sequence may include up to five amino acid alterations per each 100 amino acids of the reference amino acid of SEQ ID NO:2, 4, 6, 8 and/or 10. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous groups within the reference sequence. Again, as noted above, RNA editing may result in a codon change which will result in an expressed protein which differs in "identity" from other proteins expressed from "non-RNA edited" transcripts, which correspond directly to the open reading frame of the genomic sequence.

The present invention also relates to recombinant vectors and recombinant hosts, both prokaryotic and eukaryotic, which contain the substantially purified nucleic acid molecules disclosed throughout this specification. The nucleic acid molecules of the present invention encoding a SaGluCl channel protein, in whole or in part, can be linked with other DNA molecules, i.e, DNA molecules to which the SaGluCl coding sequence are not naturally linked, to form "recombinant DNA molecules" which encode a respective SaGluCl channel protein. The novel DNA sequences of the present invention can be inserted into vectors which comprise nucleic acids encoding SaGluCl or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a SaGluCl channel protein. It is well within the purview of the skilled artisan to determine an appropriate vector for a particular gene transfer or other use.

Included in the present invention are DNA sequences that hybridize to SEQ ID NOs:1, 3, 5, 7 and 9 under stringent conditions. By way of example, and not limitation, a procedure using conditions of high stringency is as follows: Prehybridization of filters containing DNA is carried out for 2 hours to overnight at 65° C. in buffer composed of 6×SSC, 5× Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5–20×$10^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5× Denhardt's solution, 50% formamide at 42° C. for 12 to 48 hours or a washing step carried out in 0.2× SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook et al., 1989, *Molecular Cloning: A Laboratory Manual*; Cold Spring Harbor Laboratory, Cold Spring Harbor, N.Y. In addition to the foregoing, other conditions of high stringency which may be used are well known in the art.

The present invention also relates to a substantially purified form of a respective SaGluCl channel protein, which comprises the amino acid sequence disclosed in FIGS. 2A–B and as set forth in SEQ ID NOs:2, 4, 6, 8 and 10. The disclosed SaGluCl proteins contain an open reading frame of 513 (SEQ ID NOs: 2 and 4), 462 amino acids (SEQ ID NOs:

6 and 8) and 447 (SEQ ID NO:10) amino acids in length, as shown in FIGS. 2A–B, and as follows:

MMSDLCKTPW WLCALLLLAA NVPDAWCTQQ KMNFREKEKQ VLDQILGPGR YDARIRPSGI NGTADNPTIV KVNIFLRSIS KIDDYKMMFR CAAPLACRPD PARRPRPSVM CFVTRVLNRS QAHRPGRQSG AACATPNKEY SVQLTFREQW MDERLKFNDF KGKIKYLTLT DANRVWMPDL FFSNEKEGHF HNIIMPNVYI RIFPYGSVLY SIRISLTLSC PMNLKLYPLD RQVCSLRMAS YGWTTDDLVF LWKDGDPVQV VKNLHLPRFT LEKFLTDYCN SKTNTGEYSC LKVDLLFKRE FSYYLIQIYI PCCMLVIVSW VSFWLDQSAI PARVSLGVTT LLTMATQTSG INASLPPVSY TKAIDVWTGV CLTFVFGALL EFALVNYASR SDMHRENMKK QRRQVELEHA AQLEAAADLL VEDGSTTFAM KPLVGHPGGP AAAAPGLAGL DKVRQCEIHM QPKRENCCRT WLSKFPTRSK RIDVISRITF PLVFALFNLV YWSTYLFRED ERE (SEQ ID NO:2);

MMSDLCKTPW WLCALLLLAA NVPDAWCTQQ KMNFREKEKQ VLDQILGPGR YDARIRPSGI NGTADNPTIV KVNIFLRSIS KIDDYKMMFR CAAPLACRPD PARRPRPSVM CFVTRVLNRS QAHRPGRQSG AACATPNKEY SVQLTFREQW MDERLKFNDF KGKIKYLTLT DANRVWMPDL FFSNEKEGHF HNIIMPNVYI RIFPYGSVLY SIRISLTLSC PMNLKLYPLD RQVCSLRMAS YGWTTDDLVF LWKDGDPVQV VKNLHLPRFT LEKFLTDYCN SKTNTGEYSC LKVDLLFKRE FSYYLIQIYI PCCMLVIVSW VSFWLDQSAI PARVSLGVTT LLTMATQTSG INASLPPVSY TKAIDVWTGV CLTFVFGALL EFALVNYASR SDMHRENMKK QRRQVELEHA AQLEAAADLL VEDGSTTFAM KPLVGHPGGP AAAAPGLAGL DKVRQCEIHM QPKRENCCRT WLSKFPTRSK RIDVISRITF PLVFALFNLV YWSTYLFRED DRE (SEQ ID NO:4);

MMSDLCKTPW WLCALLLLAA NVPDAWCTQQ KMNFREKEKQ VLDQILGPGR YDARIRPSGI NGTADNPTIV KVNIFLRSIS KIDDYKMEYS VQLTFREQWM DERLKFNDFK GKIKYLTLTD ANRVWMPDLF FSNEKEGHFH NIIMPNVYIR IFPYGSVLYS IRISLTLSCP MNLKLYPLDR QVCSLRMASY GWTTDDLVFL WKDGDPVQVV KNLHLPRFTL EKFLTDYCNS KTNTGEYSCL KVDLLFKREF SYYLIQIYIP CCMLVIVSWV SFWLDQSAIP ARVSLGVTTL LTMATQTSGI NASLPPVSYT KAIDVWTGVC LTFVFGALLE FALVNYASRS DMHRENMKKQ RRQVELEHAA QLEAAADLLV EDGSTTFAMK PLVGHPGGPA AAAPGLAGLD KVRQCEIHMQ PKRENCCRTW LSKFPTRSKR IDVISRITFP LVFALFNLVY WSTYLFREDE RE (SEQ ID NO:6);

MMSDLCKTPW WLCALLLLAA NVPDAWCTQQ KMNFREKEKQ VLDQILGPGR YDARIRPSGI NGTADNPTIV KVNIFLRSIS KIDDYKMEYS VQLTFREQWM DERLKFNDFK GKIKYLTLTD ANRVWMPDLF FSNEKEGHFH NIIMPNVYIR IFPYGSVLYS IRISLTLSCP MNLKLYPLDR QVCSLRMASY GWTTDDLVFL WKDGDPVQVV KNLHLPRFTL EKFLTDYCNS KTNTGEYSCL KVDLLFKREF SYYLIQIYIP CCMLVIVSWV SFWLDQSAIP ARVSLGVTTL LTMATQTSGI NASLPPVSYT KAIDVWTGVC LTFVFGALLE FALVNYASRS DMHRENMKKQ RRQVELEHAA QLEAAADLLV EDGSTTFAMK PLVGHPGGPA AAAPGLAGLD KVRQCEIHMQ PKRENCCRTW LSKFPTRSKR IDVISRITFP LVFALFNLVY WSTYLFREDD RE (SEQ ID NO:8); and, MLSATPSKLR RFCALVLLVV NLSKVTCSDQ KTNIREAERQ VMEHVLSPSR YDARLRPPGY NGTESPTVVK VNIFVRSISR VDDQHMEYDA QLTFREQWFD DRLKFDDFGG KIKYLTLTDP SRIWMPDLFF SNEKKAHFHD VVMPNVYVRI FPLGSVLYST RISMTLSCPM DLRLYPHDRQ VCSIRMASYG WTTEDLVFMW KDGDPVQVVK NLRLPRFTLE KFVTDYCHAR TNTGEYSCLK VELVFKREFR YYMVHIYIPT FMLVIVSWLS FWLDQRAITA RTCLVVTTVL TITIQTSGVR KSLPVVNYVM AVEVWLGMCV SFVFGALLQL ALVNYLARKE ACRGAAKRHN RLVGPEHSAQ LEEISEALVE DGSAAFAMKL LEEQSNSPTA DKEAAAQGGR CSPRQWWRSW MASFPTGSQR ADAASRVLFP LAFSLFCLAY WCVNASG (SEQ ID NO:10).

The present invention also relates to biologically active fragments and/or mutants of the SaGluCl protein comprising the amino acid sequence as set forth in SEQ ID NOs:2, 4, 6, 8, and 10, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of SaGluCl function.

Another preferred aspect of the present invention relates to a substantially purified, fully processed GluCl channel protein obtained from a recombinant host cell containing a DNA expression vector comprises a nucleotide sequence as set forth in SEQ ID NOs: 1, 3, 5, 7, and/or 9 and expresses the respective SaGluCl precursor protein. It is especially preferred is that the recombinant host cell be a eukaryotic host cell, such as a mammalian cell line, or *Xenopus* oocytes, as noted above.

As with many proteins, it is possible to modify many of the amino acids of SaGluCl channel protein and still retain substantially the same biological activity as the wild type protein. Thus this invention includes modified SaGluCl polypeptides which have amino acid deletions, additions, or substitutions but that still retain substantially the same biological activity as a respective, corresponding SaGluCl. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, *Science* 244:1081–1085). Accordingly, the present invention includes polypeptides where one amino acid substitution has been made in SEQ ID NO:2, 4, 6, 8 and/or 10 wherein the polypeptides still retain substantially the same biological activity as a corresponding SaGluCl protein. The present invention also includes polypeptides where two or more amino acid substitutions have been made in SEQ ID NO:2, 4, 6, 8 or 10 wherein the polypeptides still retain substantially the same biological activity as a corresponding SaGluCl protein. In particular, the present invention includes embodiments where the above-described substitutions are conservative substitutions.

One skilled in the art would also recognize that polypeptides that are functional equivalents of SaGluCl and have changes from the SaGluCl amino acid sequence that are small deletions or insertions of amino acids could also be produced by following the same guidelines, (i.e, minimizing the differences in amino acid sequence between SaGluCl and related proteins. Small deletions or insertions are generally in the range of about 1 to 5 amino acids. The effect of such small deletions or insertions on the biological activity of the modified SaGluCl polypeptide can easily be assayed by producing the polypeptide synthetically or by making the required changes in DNA encoding SaGluCl and then expressing the DNA recombinantly and assaying the protein produced by such recombinant expression.

The present invention also includes truncated forms of SaGluCl which contain the region comprising the active site of the enzyme. Such truncated proteins are useful in various assays described herein, for crystallization studies, and for structure-activity-relationship studies.

The present invention also relates to crude or substantially purified subcellular membrane fractions from the recombinant host cells (both prokaryotic and eukaryotic as well as both stably and transiently transformed cells) which contain the nucleic acid molecules of the present invention. These recombinant host cells express SaGluCl or a functional equivalent, which becomes post translationally associated with the cell membrane in a biologically active fashion. These subcellular membrane fractions will comprise either wild-type or mutant forms of SaGluCl at levels substantially above endogenous levels and hence will be useful in assays to select modulators of SaGluCl proteins or channels. In other words, a specific use for such subcellular membranes involves expression of SaGluCl within the recombinant cell followed by isolation and substantial purification of the membranes away from other cellular components and subsequent use in assays to select for modulators, such as agonist or antagonists of the protein or biologically active channel comprising one or more of the proteins disclosed herein. Therefore, another preferred aspect of the present invention relates to a substantially purified membrane preparation which has been obtained from a recombinant host cell transformed or transfected with a DNA expression vector which comprises and appropriately expresses a complete open reading frame as set forth in SEQ ID NOs: 1, 3, 5, 7, and/or 9, resulting in a functional, processed form of the respective SaGluCl channel. It is especially preferred is that the recombinant host cell be a eukaryotic host cell, such as a mammalian cell line, or *Xenopus* oocytes, as noted above.

The present invention also relates to isolated nucleic acid molecules which are fusion constructions expressing fusion proteins useful in assays to identify compounds which modulate wild-type SaGluCl activity, as well as generating antibodies against SaGluCl. One aspect of this portion of the invention includes, but is not limited to, glutathione S-transferase (GST)-SaGluCl fusion constructs. Recombinant GST-SaGluCl fusion proteins may be expressed in various expression systems, including *Spodoptera frugiperda* (Sf21) insect cells (Invitrogen) using a baculovirus expression vector (pAcG2T, Pharmingen). Another aspect involves SaGluCl1 and/or SaGlu-2 fusion constructs linked to various markers, including but not limited to GFP (Green fluorescent protein), the MYC epitope, and GST. Again, any such fusion constructs may be expressed in the cell line of interest and used to screen for modulators of one or more of the SaGluCl proteins disclosed herein.

A preferred aspect for screening for modulators of SaGluCl channel activity is an expression system for the electrophysiological-based assays for measuring glutamate-gated chloride channel activity comprising injecting the DNA molecules of the present invention into *Xenopus laevis* oocytes. The general use of *Xenopus* oocytes in the study of ion channel activity is known in the art (Dascal, 1987, *Crit. Rev. Biochem.* 22: 317–317; Lester, 1988, *Science* 241: 1057–1063; see also *Methods of Enzymology*, Vol. 207, 1992, Ch. 14–25, Rudy and Iverson, ed., Academic Press, Inc., New York). A portion of the present invention discloses an improved method of measuring channel activity and modulation by agonists and/or antagonists which is several-fold more sensitive than previously disclosed. The *Xenopus* oocytes are injected with nucleic acid material, including but not limited to DNA, mRNA or cRNA which encode a gated-channel, wherein channel activity may be measured as well as response of the channel to various modulators. Ion channel activity is measured by utilizing a holding potential more positive than the reversal potential for chloride (i.e, greater than −30 mV), preferably about 0 mV. This alteration in assay measurement conditions has resulting in a 10-fold increase in sensitivity of the assay to modulation by ivermectin phosphate. Therefore, this improved assay allows screening and selecting for compounds which modulate GluCl activity at levels which were previously thought to be undetectable. This procedure is outlined in the Example section. It will be evident to the skilled artisan that this method may be utilized in various ion channel measurement assays, and especially assays which measure glutamate-gated activity in a eukaryotic cell, such as a *Xenopus* oocyte. It is especially preferred that invertebrate glutamate-gated chloride channels, including but in no way limited to *Caenorhabditis elegans, Drosophila melonogaster, Ctenocephalides felis* glutamate-gated channels as well as the *S. americana* glutamate-gated channel proteins disclosed herein, may be utilized in an assay to screen and select for compounds which modulate the activity of these channels. Levels of SaGluCl protein in host cells are quantified by immunoaffinity and/or ligand affinity techniques. Cells expressing SaGluCl can be assayed for the number of GluCl molecules expressed by measuring the amount of radioactive glutamate or ivermectin binding to cell membranes. SaGluCl-specific affinity beads or SaGluCl-specific antibodies are used to isolate for example $^{35}$S-methionine labeled or unlabelled SaGluCl protein. Labeled SaGluCl protein is analyzed by SDS-PAGE. Unlabelled SaGluCl protein is detected by Western blotting, ELISA or RIA assays employing SaGluCl specific antibodies.

Any of a variety of procedures may be used to clone SaGluCl. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of SaGluCl cDNA. These gene-specific primers are designed through identification of an expressed sequence tag (EST) nucleotide sequence which has been identified by searching any number of publicly available nucleic acid and protein databases; (2) direct functional expression of the SaGluCl cDNA following the construction of a SaGluCl-containing cDNA library in an appropriate expression vector system; (3) screening a SaGluCl-containing cDNA library constructed in a bacteriophage or plasmid shuttle vector with a labeled degenerate oligonucleotide probe designed from the amino acid sequence of the SaGluCl protein; (4) screening a SaGluCl-containing cDNA library constructed in a bacteriophage or plasmid shuttle vector with a partial cDNA encoding the SaGluCl protein. This partial cDNA is obtained by the specific PCR amplification of SaGluCl DNA fragments through the design of degenerate oligonucleotide primers from the amino acid sequence known for other kinases which are related to the SaGluCl protein; (5) screening a SaGluCl-containing cDNA library constructed in a bacteriophage or plasmid shuttle vector with a partial cDNA or oligonucleotide with homology to a mammalian SaGluCl protein. This strategy may also involve using gene-specific oligonucleotide primers for PCR amplification of SaGluCl cDNA identified as an EST as described above; or (6) designing 5' and 3' gene specific oligonucleotides using SEQ ID NO: 1, 3, 5, 7, or 9 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding SaGluCl.

It is readily apparent to those skilled in the art that other types of libraries, as well as libraries constructed from other cell types-or species types, may be useful for isolating a SaGluCl-encoding DNA or a SaGluCl homologue. Other types of libraries include, but are not limited to, cDNA libraries derived from other cells.

It is readily apparent to those skilled in the art that suitable cDNA libraries may be prepared from cells or cell lines which have SaGluCl activity. The selection of cells or cell lines for use in preparing a cDNA library to isolate a cDNA encoding SaGluCl may be done by first measuring cell-associated SaGluCl activity using any known assay available for such a purpose.

Preparation of cDNA libraries can be performed by standard techniques well known in the art. Well known cDNA library construction techniques can be found for example, in Sambrook et al., 1989*, Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding SaGluCl may also be isolated from a suitable genomic DNA library. Construction of genomic DNA libraries can be performed by standard techniques well known in the art. Well known genomic DNA library construction techniques can be found in Sambrook, et al., supra. One may prepare genomic libraries, especially in P1 artificial chromosome vectors, from which genomic clones containing the SaGluCl can be isolated, using probes based upon the SaGluCl nucleotide sequences disclosed herein. Methods of preparing such libraries are known in the art (Ioannou et al., 1994*, Nature Genet.* 6:84–89).

In order to clone a SaGluCl gene by one of the preferred methods, the amino acid sequence or DNA sequence of a SaGluCl or a homologous protein may be necessary. To accomplish this, a respective SaGluCl channel protein may be purified and the partial amino acid sequence determined by automated sequenators. It is not necessary to determine the entire amino acid sequence, but the linear sequence of two regions of 6 to 8 amino acids can be determined for the PCR amplification of a partial SaGluCl DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the SaGluCl sequence but others in the set will be capable of hybridizing to SaGluCl DNA even in the presence of DNA oligonucleotides with mismatches. The mismatched DNA oligonucleotides may still sufficiently hybridize to the SaGluCl DNA to permit identification and isolation of SaGluCl encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, 3, 5, 7 or 9 either for the purpose of isolating overlapping 5' and 3' RACE products for generation of a full-length sequence coding for SaGluCl, or to isolate a portion of the nucleotide sequence coding for SaGluCl for use as a probe to screen one or more cDNA- or genomic-based libraries to isolate a full-length sequence encoding SaGluCl or SaGluCl-like proteins.

This invention also includes vectors containing a SaGluCl gene, host cells containing the vectors, and methods of making substantially pure SaGluCl protein comprising the steps of introducing the SaGluCl gene into a host cell, and cultivating the host cell under appropriate conditions such that SaGluCl is produced. The SaGluCl so produced may be harvested from the host cells in conventional ways. Therefore, the present invention also relates to methods of expressing the SaGluCl protein and biological equivalents disclosed herein, assays employing these gene products, recombinant host cells which comprise DNA constructs which express these proteins, and compounds identified through these assays which act as agonists or antagonists of SaGluCl activity.

The cloned SaGluCl cDNA obtained through the methods described above may be recombinantly expressed by molecular cloning into an expression vector (such as pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce recombinant SaGluCl. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the SaGluCl cDNA sequence(s) that yields optimal levels of SaGluCl, cDNA molecules including but not limited to the following can be constructed: a cDNA fragment containing the full-length open reading frame for SaGluCl as well as various constructs containing portions of the cDNA encoding only specific domains of the protein or rearranged domains of the protein. All constructs can be designed to contain none, all or portions of the 5' and/or 3' untranslated region of a SaGluCl cDNA. The expression levels and activity of SaGluCl can be determined following the introduction, both singly and in combination, of these constructs into appropriate host cells. Following determination of the SaGluCl cDNA cassette yielding optimal expression in transient assays, this SaGluCl cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al., supra, are well known and available to the artisan of ordinary skill in the art. Therefore, another aspect of the present invention includes host cells that have been engineered to contain and/or express DNA sequences encoding the SaGluCl. An expression vector containing DNA encoding a SaGluCl-like protein may be used for expression of SaGluCl in a recombinant host cell. Such recombinant host cells can be cultured under suitable conditions to produce SaGluCl or a biologically equivalent form. Expression vectors may include, but are not limited to, cloning vectors, modified cloning vectors, specifically designed plasmids or viruses. Commercially available mammalian expression vectors which may be suitable for recombinant SaGluCl expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAI-amp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565). Also, a variety of bacterial expression vectors may be used to express recombinant SaGluCl in bacterial cells. Commercially available bacterial expression vectors which may be suitable for recombinant SaGluCl expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant SaGluCl in fungal cells. Commercially available fungal cell expression vectors which may be suitable for recombinant SaGluCl expression include but are not limited to pYES2 (Invitrogen) and *Pichia* expression vector (Invitrogen). Also, a variety of insect cell expression vectors may be used to express recombinant protein in insect cells. Commercially available insect cell expression vectors which may be suitable for recombinant expression of SaGluCl include but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M($TK^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

As noted above in regard to the use of *Xenopus* oocytes to express a SaGluCl gene of interest, the present invention is directed to methods for screening for compounds which modulate the expression of DNA or RNA encoding a SaGluCl protein. Compounds which modulate these activities may be DNA, RNA, peptides, proteins, or non-proteinaceous organic molecules. Compounds may modulate by increasing or attenuating the expression of DNA or RNA encoding SaGluCl, or the function of the SaGluCl-based channels. Compounds that modulate the expression of DNA or RNA encoding SaGluCl or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing SaGluCl, antibodies to SaGluCl, or modified SaGluCl may be prepared by known methods for such uses.

The DNA molecules, RNA molecules, recombinant protein and antibodies of the present invention may be used to screen and measure levels of SaGluCl. The recombinant proteins, DNA molecules, RNA molecules and antibodies lend themselves to the formulation of kits suitable for the detection and typing of SaGluCl. Such a kit would comprise a compartmentalized carrier suitable to hold in close confinement at least one container. The carrier would further comprise reagents such as recombinant SaGluCl or anti-SaGluCl antibodies suitable for detecting SaGluCl. The carrier may also contain a means for detection such as labeled antigen or enzyme substrates or the like.

The assays described herein can be carried out with cells that have been transiently or stably transfected with SaGluCl. The expression vector may be introduced into host cells via any one of a number of techniques including but not limited to transformation, transfection, protoplast fusion, and electroporation. Transfection is meant to include any method known in the art for introducing SaGluCl into the test cells. For example, transfection includes calcium phosphate or calcium chloride mediated transfection, lipofection, infection with a retroviral construct containing SaGluCl, and electroporation. The expression vector-containing cells are individually analyzed to determine whether they produce SaGluCl protein. Identification of SaGluCl expressing cells may be done by several means, including but not limited to immunological reactivity with anti-SaGluCl antibodies, labeled ligand binding, the presence of host cell-associated SaGluCl activity via ligand binding.

The specificity of binding of compounds showing affinity for SaGluCl is shown by measuring the affinity of the compounds for recombinant cells expressing the cloned receptor or for membranes from these cells. Expression of the cloned receptor and screening for compounds that bind to SaGluCl or that inhibit the binding of a known, radiolabeled ligand of SaGluCl to these cells, or membranes prepared from these cells, provides an effective method for the rapid selection of compounds with high affinity for SaGluCl. Such ligands need not necessarily be radiolabeled but can also be nonisotopic compounds that can be used to displace bound radiolabeled compounds or that can be used as activators in functional assays. Compounds identified by the above method are likely to be agonists or antagonists of SaGluCl and may be peptides, proteins, or non-proteinaceous organic molecules.

Accordingly, the present invention is directed to methods for screening for compounds which modulate the expression of DNA or RNA encoding a SaGluCl protein as well as compounds which effect the function of the SaGluCl protein. Methods for identifying agonists and antagonists of other receptors are well known in the art and can be adapted to identify agonists and antagonists of SaGluCl. For example, Cascieri et al. (1992, *Molec. Pharmacol.* 41:1096–1099) describe a method for identifying substances that inhibit agonist binding to rat neurokinin receptors and thus are potential agonists or antagonists of neurokinin receptors.

The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to is measured, such binding can be measured by employing a labeled substance or agonist. The substance or agonist can be labeled in any convenient manner known to the art, e.g., radioactively, fluorescently, enzymatically.

Therefore, the specificity of binding of compounds having affinity for SaGluCl shown by measuring the affinity of the compounds for recombinant cells expressing the cloned receptor or for membranes from these cells. Expression of the cloned receptor and screening for compounds that bind to SaGluCl or that inhibit the binding of a known, radiolabeled ligand of SaGluCl (such as glutamate, ivermectin or nodulasporic acid) to these cells, or membranes prepared from these cells, provides an effective method for the rapid selection of compounds with high affinity for SaGluCl. Such ligands need not necessarily be radiolabeled but can also be nonisotopic compounds that can be used to displace bound radiolabeled compounds or that can be used as activators in functional assays. Compounds identified by the above method again are likely to be agonists or antagonists of SaGluCl and may be peptides, proteins, or non-proteinaceous organic molecules. As noted elsewhere in this specification, compounds may modulate by increasing or attenuating the expression of DNA or RNA encoding SaGluCl, or by acting as an agonist or antagonist of the SaGluCl receptor protein. Again, these compounds that modulate the expression of DNA or RNA encoding SaGluCl or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample.

To this end, the present invention relates in part to methods of identifying a substance which modulates SaGluCl1 and/or SaGluCl2 receptor activity, which involves:

(a) combining a test substance in the presence and absence of a SaGluCl1 and/or SaGluCl2 receptor protein wherein said receptor protein comprises the amino acid sequence as set forth in SEQ ID NO:2, 4, 6, 8 and/or 10 and, (b) measuring and comparing the effect of the test substance in the presence and absence of the SaGluCl1 and/or SaGluCl2 receptor protein.

In addition, several specific embodiments are disclosed herein to show the diverse type of screening or selection assay which the skilled artisan may utilize in tandem with expression vectors directing the expression of the SaGluCl1 and/or SaGluCl2 receptor protein and an additional SaGluCl. Methods for identifying agonists and antagonists of other receptors are well known in the art and can be adapted to identify agonists and antagonists of SaGluCl1 and/or SaGluCl2. Therefore, these embodiments are presented as examples and not as limitations. To this end, the present invention includes assays by which SaGluCl and/or SaGluCl2 modulators (such as agonists and antagonists) may be identified. Accordingly, the present invention includes a method for determining whether a substance is a potential agonist or antagonist of SaGluCl1 and/or SaGluCl2 that comprises:

(a) transfecting or transforming cells with an expression vector that directs expression of SaGluCl and/or SaGluCl2 in the cells;

(b) transfecting or transforming said cells with a second expression vector that directs expression of a known GluCl subunit which co-assembles with SaGluCl1 and/or SaGluCl2 resulting in test cells;

(c) allowing the test cells to grow for a time sufficient to allow SaGluCl1 and/or SaGluCl2 to be expressed and for a functional channel to be generated;

(d) exposing the cells to a labeled ligand of SaGluCl1 and/or SaGluCl2 in the presence and in the absence of the substance;

(e) measuring the binding of the labeled ligand to the SaGluCl and/or SaGluCl2 channel; where if the amount of binding of the labeled ligand is less in the presence of the substance than in the absence of the substance, then the substance is a potential agonist or antagonist of SaGluCl1 and/or SaGluCl2.

The conditions under which step (d) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (d) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to SaGluCl1 and/or SaGluCl2, i.e., whether the substance is a potential agonist or an antagonist of SaGluCl1 and/or SaGluCl2 channel activation, where the method comprises:

(a) transfecting or transforming cells with an expression vector that directs the expression of SaGluCl1 and/or SaGluCl2 in the cells;

(b) transfecting or transforming said cells with a second expression vector that directs expression of at least one other known GluCl subunit which co-assembles with SaGluCl1 and/or SaGluCl2 resulting in test cells;

(c) exposing the test cells to the substance;

(d) measuring the amount of binding of the substance to SaGluCl1 and/or SaGluCl2;

(e) comparing the amount of binding of the substance to SaGluCl1 and/or SaGluCl2 in the test cells with the amount of binding of the substance to control cells that have not been transfected with SaGluCl1 and/or SaGluCl2;

wherein if the amount of binding of the substance is greater in the test cells as compared to the control cells, the substance is capable of binding to SaGluCl1 and/or SaGluCl2. Determining whether the substance is actually an agonist or antagonist can then be accomplished by the use of functional assays such as, e.g., the assay involving the use of promiscuous G-proteins described below.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

Expression of SaGluCl DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of SaGluCl in a host cell, SaGluCl protein may be recovered to provide SaGluCl protein in active form. Several SaGluCl protein purification procedures are available and suitable for use. Recombinant SaGluCl protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant SaGluCl protein can be separated from other cellular proteins by use of an immunoaffinity column made with monoclonal or polyclonal antibodies specific for full-length SaGluCl protein, or polypeptide fragments of SaGluCl protein.

Polyclonal or monoclonal antibodies may be raised against SaGluCl or a synthetic peptide (usually from about 9 to about 25 amino acids in length) from a portion of SaGluCl1 or SaGluCl2 as disclosed in SEQ D NOs:2, 4, 6, 8 and/or 10. Monospecific antibodies to SaGluCl are purified from mammalian antisera containing antibodies reactive against SaGluCl or are prepared as monoclonal antibodies reactive with SaGluCl using the technique of Kohler and Milstein (1975, *Nature* 256: 495–497). Monospecific antibody as used herein is defined as a single antibody species or multiple antibody species with homogenous binding characteristics for SaGluCl. Homogenous binding as used herein refers to the ability of the antibody species to bind to a specific antigen or epitope, such as those associated with SaGluCl, as described above. Human SaGluCl-specific antibodies are raised by immunizing animals such as mice, rats, guinea pigs, rabbits, goats, horses and the like, with an appropriate concentration of SaGluCl protein or a synthetic peptide generated from a portion of SaGluCl with or without an immune adjuvant.

Preimmune serum is collected prior to the first immunization. Each animal receives between about 0.1 mg and about 1000 mg of SaGluCl protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of SaGluCl protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of SaGluCl in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with SaGluCl are prepared by immunizing inbred mice, preferably Balb/c, with SaGluCl protein. The mice are immunized by the IP or SC route with about 1 mg to about 100 mg, preferably about 10 mg, of SaGluCl protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of SaGluCl in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using SaGluCl as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-SaGluCl mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of SaGluCl in body fluids or tissue and cell extracts.

It is readily apparent to those skilled in the art that the above described methods for producing monospecific antibodies may be utilized to produce antibodies specific for SaGluCl peptide fragments, or a respective full-length SaGluCl.

SaGluCl antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length SaGluCl or SaGluCl protein fragments are slowly passed through the column. The column is then washed with phosphate buffered saline until the optical density ($A_{280}$) falls to background, then the protein is eluted with 0.23 M glycine-HCl (pH 2.6). The purified SaGluCl protein is then dialyzed against phosphate buffered saline.

The present invention also relates to a non-human transgenic animal which is useful for studying the ability of a variety of compounds to act as modulators of either SaGluCl1, SaGluCl2, or any alternative functional SaGluCl channel in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art (e.g., U.S. Pat. No. 5,612,205; U.S. Pat. No. 5,721,367, U.S. Pat. No. 5,464,764, U.S. Pat. No. 5,487,992, U.S. Pat. No. 5,627,059, U.S. Pat. No. 5,631,153). Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art. A type of target cell for transgene introduction is the embryonic stem cell (ES). ES cells can be obtained from pre-implantation embryos cultured in vitro and fused with embryos (Evans et al., 1981, *Nature* 292:154–156; Bradley et al., 1984, *Nature* 309:255–258; Gossler et al., 1986, *Proc. Natl. Acad. Sci.* USA 83:9065–9069; and Robertson et al., 1986 *Nature* 322:445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468–1474). It will also be within the purview of the skilled artisan to produce transgenic or knock-out ivertebrate animals (e.g., *C. elegans*) which express the SaGluCl2 transgene in a wild type *C. elegans* GluCl background as well in *C. elegans* mutants knocked out for one or both of the *C. elegans* GluCl subunits. These organisms will be helpful in further determining the dominant negative effect of SaGluCl2 as well as selecting from compounds which modulate this effect.

Pharmaceutically useful compositions comprising modulators of SaGluCl may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified SaGluCl, or either SaGluCl agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation and Characterization of DNA Molecules Encoding SaGluCl

The molecular procedures were performed following standard procedures well known in the art available in references such as Ausubel et. al. (1992, Short protocols in molecular biology. F. M. Ausubel et al., —$2^{nd}$. ed. (John Wiley & Sons)) and Sambrook et al. (1989, Molecular cloning. A laboratory manual. J. Sambrook, E. F. Fritsch, and T. Maniatis—$2^{nd}$ ed. (Cold Spring Harbor Laboratory Press)). RNA was isolated from neurons dissected out of grasshopper ventral ganglia, using TRI-REAGENT (Molec. Res. Inc.). First strand cDNA was synthesized from 200 ng RNA using a SUPERSCRIPT preamplification System (Life Technologies). A tenth of the first strand reaction was used for PCR. The degenerate oligos utilized were designed based on sequences obtained from *C. elegans, Drosophila*, and Flea (*C. felis*) GluCls:

The oligonucleotides used are as follows:

Forward (Oligo 27F2):

GGAT(G/T)CCNGA(C/T)N(C/T)NTT(C/T)TTNN(A/C) NA(A/C)(C/T)G (SEQ ID NO:11)

Reverse 1 (Oligo 3B):

CNA(A/G)(A/C)A(A/G)NGCNC(A/C)GAANA(C/T)(A/G) AA(C/T)G (SEQ ID NO:12)

Reverse 2 (Oligo 3A):

CAN(A/G)CNCCN(A/G)(G/T)CCANAC(A/G)TCNA(C/T)N(A/G)C (SEQ ID NO:13)

Two PCR rounds, using the combinations 27F2+3A, then 27F2+3B" were performed.

The cycles were as follow: 1×(95° C. for 120 sec.), then 30×(95° C. for 45 sec.; 50° C. for 90 sec.; and 72° C. for 120 sec.), then 1×(72° C. for 120 sec.). Reagents were from Life Technology Inc. The oligos' concentration was 5 μM. One tenth of the PCR reaction products was tested by Southern blot analysis, in order to identify and prevent the PCR-cloning of contaminating sequence from GluCl clones already in use in the laboratory. Novel PCR products of the appropriate size were cloned into the PCR2.1 plasmid vector using a "TA" cloning kit (Invitrogen, Inc.). Following sequence analysis (ABI Prism, PE Applied Biosystems), selected PCR clone inserts were radiolabelled and used as probes to screen a cDNA library generated into the Uni-ZAP vector (Stratagene, Inc.) from using and a poly (A) enriched fraction from the RNA mentioned above. Sequences obtained from full-length cDNA clones (ABI Prism, PE Applied Biosystems) were analyzed using the GCG Inc. package. Subcloning of SaGluCl1 and of SaGluCl2 into a mammalian expression vector was done by excision of whole inserts (EcoRI+XhoI excision) from the UniZap pBS plasmid, followed by ligation into the TetSplice (Cat. No. 10583-011; Life Technologies/GIBCO BRL). FIGS. 1A–1F and FIGS. 2A–2B show the derived nucleotide and amino acid sequence covering the open reading frames for SaGluCl1 and SaGluCl2 cDNA clones.

EXAMPLE 2

Functional Eexpression of GluCls Clones in *Xenopus* Oocytes

Full length cDNA clones corresponding to the selected RT-PCR sequences were used as template for synthesis of in vitro transcribed RNA (Ambion Inc.). The full-length cDNA encoding SaGluCl1 in a Bluescript plasmid is linearized and capped cRNA transcripts are synthesized using appropriate oligonucleotide primers and the mMESSAGE mMACHINE in vitro RNA transcription kit from Ambion. *Xenopus laevis* oocytes were prepared and injected using standard methods as described (Arena et al., 1991*, Mol. Pharmacol.* 40: 368–374; Arena et al, 1992*, Mol. Brain Res.* 15: 339–348). Adult female *Xenopus laevis* were anesthetized with 0.17% tricaine methanesulfonate and the ovaries were surgically removed and placed in a dish consisting of (mM): NaCl 82.5, KCl 2, $MgCl_2$ 1, $CaCl_2$ 1.8, HEPES 5, adjusted to pH 7.5 with NaOH(OR-2). Ovarian lobes were broken open, rinsed several times, and gently shaken in OR-2 containing 0.2% collagenase (Sigma, Type 1A) for 2–5 hours. When approximately 50% of the follicular layers were removed, Stage V and VI oocytes were selected and placed in media consisting of (mM): NaCl 86, KCl 2, $MgCl_2$ 1, $CaCl_2$ 1.8, HEPES 5, Na pyruvate 2.5, theophylline 0.5, gentamicin 0.1 adjusted to pH 7.5 with NaOH (ND-96) for 24–48 hours before injection. For most experiments, oocytes were injected with 10 ng of cRNA in 50 nl of RNase free water. Control oocytes were injected with 50 nl of water. Oocytes were incubated for 1–5 days in ND-96 supplemented with 50 mg/ml gentamycin, 2.5 mM Na pyruvate and 0.5 mM theophylline before recording. Incubations and collagenase digestion were carried out at 18° C.

Voltage-clamp studies were conducted with the two microelectrode voltage clamp technique using a Dagan CA1 amplifier (Dagan Instruments, Minneapolis, Minn.). The current passing microelectrodes were filled with 0.7 M KCl plus 1.7 M $K_3$-citrate and the voltage recording microelectrodes were filled with 1.0 M KCl. The extracellular solution for most experiments was saline consisting of (mM): NaCl 96, $BaCl_2$ 3.5, $MgCl_2$ 0.5, $CaCl_2$ 0.1, HEPES 5, adjusted to pH 7.5 with NaOH. The extracellular chloride concentration was reduced in some experiments by equimolar replacement of NaCl with the sodium salt of the indicated anion. Experiments were conducted at 21–24° C. Data were acquired using the program Pulse and most analysis was performed with the companion program Pulsefit (Instrutech Instruments, Great Neck, N.Y.) or with Igor Pro (Wavemetrics, Lake Oswego, Oreg.). Data were filtered ($f_c$, −3 db) at 1 kHz, unless otherwise indicated. FIG. 3 shows the results of the experiment in which the clone SaGluCl1 (short form "SC") was expressed in a *Xenopus* oocyte. The measurement was made as described in this Example with the two microelectrode voltage clamp technique and the membrane potential was held at 0 mV. Two current recordings are superimposed. The bars at top show the duration of application of glutamate and ivermectin phosphate. Glutamate was applied first and elicited a rapidly desensitizing current. Ivermectin phosphate elicited a current of similar amplitude, but the channel stayed open much longer. This indicates that expression of this protein reconstitutes a functional ion channel that responds to both glutamate and ivermectin.

EXAMPLE 3

Functional Expression of GluCls Clones in Mammalian Cells

PTet-Splice subclones of SaGluCl1 and SaGluCl2 as disclosed in Example section 1 were transfected into CHO Tet-Off cells (Clontech labs, Inc.) using the Lipofectamine Plus reagent (Life Technologies Inc.). Stable cell lines are selected by growth in the presence of G418. Single G418 resistant clones are isolated and shown to contain the intact SaGluCl gene. Clones containing the SaGluCl cDNAs may be analyzed for expression using immunological techniques, such as immuneprecipitation, Western blot, and immunofluorescence using antibodies specific to the SaGluCl proteins. Antibody may obtained from rabbits innoculated with peptides that are synthesized from the amino acid sequence predicted from the SaGluCl sequences. Expression is also analyzed using patch clamp electrophysiological techniques, an anion flux assay, and $^3$H-ivermectin and $^3$H-glutamate binding assays.

Cells that are expressing SaGluCl stably or transiently, are used to test for expression of avermectin, glutamate, sensitive chloride channels and for ligand binding activity. These cells are used to identify and examine other compounds for their ability to modulate, inhibit or activate the avermectin, glutamate sensitive chloride channel and to compete for binding with radioactive avermectin, glutamate, derivatives. These cells are used to identify and examine other compounds which modulate SaGluCl activity with an anion flux assay.

Cassettes containing the SaGluCl cDNA in the positive orientation with respect to the promoter are ligated into appropriate restriction sites 3' of the promoter and identified by restriction site mapping and/or sequencing. These cDNA expression vectors are introduced into host cells for, example CHO cells, COS-7 (ATCC# CRL1651), and CV-1 tat [Sackevitz et al., *Science* 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants can be harvested and analyzed for SaGluCl expression.

All of the vectors used for mammalian transient expression can be used to establish stable cell lines expressing SaGluCl. Unaltered SaGluCl cDNA constructs cloned into expression vectors are expected to program host cells to make SaGluCl protein. In addition, SaGluCl is expressed extracellularly as a secreted protein by ligating SaGluCl GluCl cDNA constructs to DNA encoding the signal sequence of a secreted protein. The transfection host cells include, but are not limited to, CV-1-P [Sackevitz et al., *Science* 238: 1575 (1987)], tk-L [Wigler, et al., *Cell* 11: 223 (1977)], NS/0, and dHFr-CHO [Kaufman and Sharp, *J. Mol. Biol.* 159: 601, (1982)].

Co-transfection of any vector containing SaGluCl GluCl with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of SaGluCl GluCl are quantitated by the assays described herein.

SaGluCl cDNA constructs are also ligated into vectors containing amplifiable drug-resistance markers for the production of mammalian cell clones synthesizing the highest possible levels of SaGluCl. Following introduction of these constructs into cells, clones containing the plasmid are selected with the appropriate agent, and isolation of an over-expressing clone with a high copy number of plasmids is accomplished by selection with increasing doses of the agent.

Figure 4A:
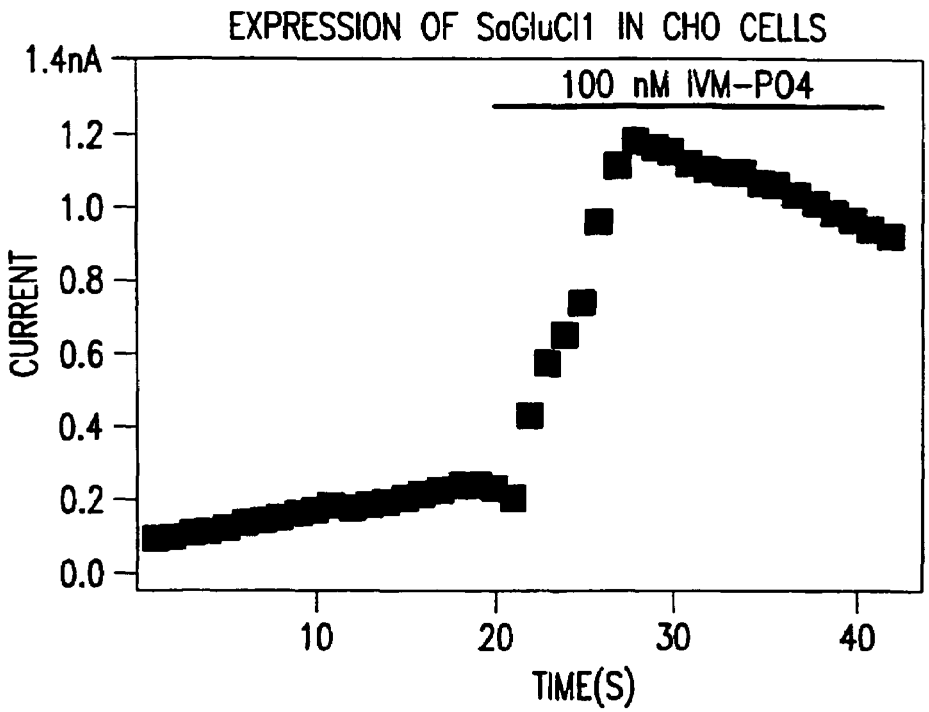
FIG. 4A and FIG. 4B show the SaGluCl1 (short form "SC") expressed in CHO cells assembles into a homomultimer and is activated by ivermectin (FIG. 4A) and nodulasporic acid (FIG. 4B). 100 nM ivermectin and 1 μM nodulasporic acid were added at 20 seconds and current was measured.
Figure 4B:
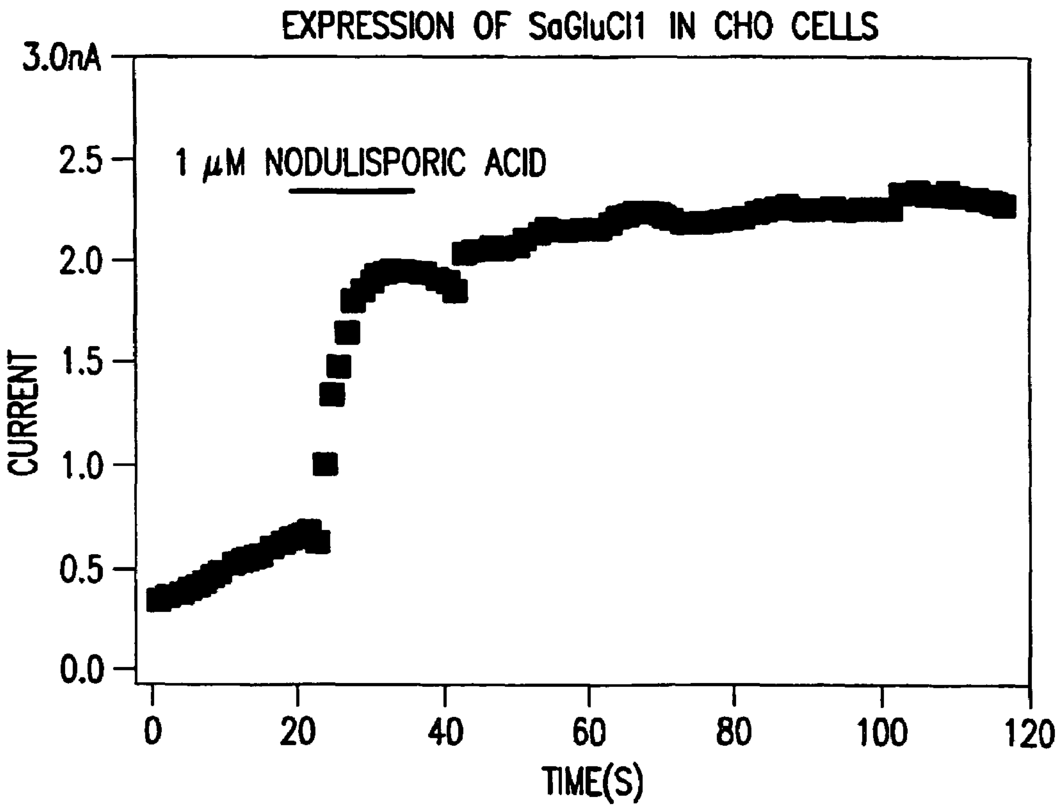

The expression of recombinant SaGluCl1 and/or SaGluCl2 is achieved by transfection of the full-length SaGluCl cDNA into a mammalian host cell described herein. Functional expression of SaGluCl1 in CHO cells is shown in FIGS. 4A and 4B, which indicates that this subunit can assemble into a homomultimer channel activated by ivermectin (IVM, FIG. 4A) and nodulasporic acid (NA, FIG. 4B).

EXAMPLE 4

Cloning of SaGluCl GluCl cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). A recombinant baculoviruse expressing SaGluCl cDNA is produced by the following standard methods (In Vitrogen Maxbac Manual): the SaGluCl cDNA constructs are ligated into the polyhedrin gene in a variety of baculovirus transfer vectors, including the pAC360 and the BlueBac vector (In Vitrogen). Recombinant baculoviruses are generated by homologous recombination following co-transfection of the baculovirus transfer vector and linearized AcNPV genomic DNA [Kitts, 1990, *Nuc. Acid. Res.* 18: 5667] into Sf9-cells. Recombinant pAC360 viruses are identified by the absence of inclusion bodies in infected cells and recombinant pBlueBac viruses are identified on the basis of b-galactosidase expression (Summers, M. D. and Smith, G. E., Texas Agriculture Exp. Station Bulletin No. 1555). Following plaque purification, SaGluCl expression is measured by the assays described herein.

The cDNA encoding the entire open reading frame for SaGluCl GluCl is inserted into the BamHI site of pBlueBacII. Constructs in the positive orientation are identified by sequence analysis and used to transfect Sf9 cells in the presence of linear AcNPV mild type DNA.

Authentic, active SaGluCl is found in the cytoplasm of infected cells. Active SaGluCl is extracted from infected cells by hypotonic or detergent lysis.

EXAMPLE 5

Cloning of SaGluCl GluCl cDNA into a Yeast Expression Vector

Recombinant SaGluCl is produced in the yeast *S. cerevisiae* following the insertion of the optimal SaGluCl cDNA cistron into expression vectors designed to direct the intracellular or extracellular expression of heterologous proteins. In the case of intracellular expression, vectors such as EmBLyex4 or the like are ligated to the SaGluCl cistron [Rinas, et al., 1990, *Biotechnology* 8: 543–545; Horowitz B. et al., 1989, *J. Biol. Chem.* 265: 4189–4192]. For extracellular expression, the SaGluCl GluCl cistron is ligated into yeast expression vectors which fuse a secretion signal (a yeast or mammalian peptide) to the $NH_2$ terminus of the SaGluCl protein [Jacobson, 1989, *Gene* 85: 511–516; Riett and Bellon, 1989, *Biochem.* 28: 2941–2949].

These vectors include, but are not limited to pAVE1-6, which fuses the human serum albumin signal to the expressed cDNA [Steep, 1990, *Biotechnology* 8: 42–46], and the vector pL8PL which fuses the human lysozyme signal to the expressed cDNA [Yamamoto, *Biochem.* 28: 2728–2732)]. In addition, SaGluCl is expressed in yeast as a fusion protein conjugated to ubiquitin utilizing the vector pVEP [Ecker, 1989, *J. Biol. Chem.* 264: 7715–7719, Sabin, 1989 *Biotechnology* 7: 705–709, McDonnell, 1989, *Mol. Cell Biol.* 9: 5517–5523 (1989)]. The levels of expressed SaGluCl are determined by the assays described herein.

EXAMPLE 6

Purification of Recombinant SaGluCl CluCl

Recombinantly produced SaGluCl may be purified by antibody affinity chromatography. SaGluCl GluCl antibody affinity columns are made by adding the anti-SaGluCl GluCl antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized SaGluCl are slowly passed through the column. The column is then washed with phosphate-buffered saline together with detergents until the optical density (A280) falls to background, then the protein is eluted with 0.23 M glycine-HCl (pH 2.6) together with detergents. The purified SaGluCl protein is then dialyzed against phosphate buffered saline.

The invention claimed is:

1. A purified DNA molecule encoding a *S. americana* GluCl1 channel protein which comprises an amino acid sequence of SEQ ID NO:8.

2. An expression vector for expressing a *S. americana* GluCl1 channel protein in a recombinant host cell wherein said expression vector comprises the DNA molecule of claim 1.

3. An isolated host cell which expresses a recombinant *S. americana* GluCl1 channel protein wherein said host cell contains the expression vector of claim 2.

4. A process for expressing a *S. americana* GluCl1 channel protein in a recombinant host cell, comprising:

(a) transfecting the expression vector of claim 2 into a suitable host cell; and, (b) culturing the host cell of step (a) under conditions which allow expression of said *S. americana* GluCl channel protein from said expression vector.

5. A purified DNA molecule encoding a *S. americana* GluCl1 channel protein which consists of an amino acid sequence as set forth in SEQ ID NO:8.

6. An expression vector for expressing a *S. americana* GluCl1 channel protein in a recombinant host cell wherein said expression vector comprises the DNA molecule of claim 5.

7. An isolated host cell which expresses a recombinant *S. americana* GluCl1 channel protein wherein said host cell contains the expression vector of claim 6.

8. A process for expressing a *S. americana* GluCl1 channel protein in a recombinant host cell, comprising:

(a) transfecting the expression vector of claim 6 into a suitable host cell; and, (b) culturing the host cell of step (a) under conditions which allow expression of said *S. americana* GluCl channel protein from said expression vector.

9. A purified DNA molecule encoding a recombinant *S. americana* GluCl1 channel protein wherein said DNA molecule comprises a nucleotide sequence of SEQ ID NO:7.

10. An expression vector for expressing a recombinant *S. americana* GluCl1 channel protein wherein said expression vector comprises the DNA molecule of claim 9.

11. An isolated host cell which expresses a recombinant *S. americana* GluCl1 channel protein wherein said host cell contains the expression vector of claim 10.

12. A process for expressing a recombinant *S. americana* GluCl1 channel protein in a recombinant host cell, comprising:

(a) transfecting the expression vector of claim 10 into a suitable host cell; and, (b) culturing the host cell of step (a) under conditions which allow expression of said recombinant *S. Americana* GluCl1 channel protein from said expression vector.

13. An isolated *S. americana* GluCl1 channel protein which comprises an amino acid sequence of SEQ ID NO:8.

14. The isolated *S. americana* GluCl1 channel protein of claim 13 which is a product of a DNA expression vector contained within an isolated recombinant host cell.

15. A substantially pure membrane preparation comprising the *S. americana* GluCl1 channel protein purified from the isolated recombinant host cell of claim 14.

16. An isolated *S. americana* GluCl1 channel protein which consists of the amino acid sequence of SEQ ID NO:8.

17. The isolated *S. americana* GluCl1 channel protein of claim 16 which is a product of a DNA expression vector contained within an isolated recombinant host cell.

18. A substantially pure membrane preparation comprising the *S. americana* GluCl1 channel protein purified from the recombinant host cell of claim 17.

* * * * *